US007349809B2

(12) United States Patent
Goodenowe

(10) Patent No.: US 7,349,809 B2
(45) Date of Patent: Mar. 25, 2008

(54) METHOD OF NON-TARGETED COMPLEX SAMPLE ANALYSIS

(75) Inventor: Dayan Burke Goodenowe, Saskatoon (CA)

(73) Assignee: Yol Bolsum Canada Inc., Saskatoon, Saskatchewan (CA)

( * ) Notice: Subject to any disclaimer, the term of this patent is extended or adjusted under 35 U.S.C. 154(b) by 0 days.

(21) Appl. No.: 10/208,276

(22) Filed: Jul. 30, 2002

(65) Prior Publication Data

US 2004/0029120 A1 Feb. 12, 2004

(30) Foreign Application Priority Data

Feb. 2, 2000 (CA) .................................... 2298181
Feb. 1, 2001 (WO) ..................... PCT/CA01/00111

(51) Int. Cl.
G01N 33/48 (2006.01)
(52) U.S. Cl. ............................. 702/19; 702/23; 707/6; 707/102
(58) Field of Classification Search ................. 702/19; 707/102
See application file for complete search history.

(56) References Cited

U.S. PATENT DOCUMENTS

| | | | | |
|---|---|---|---|---|
| 4,956,788 | A | 9/1990 | Guan et al. ................. | 363/498 |
| 4,978,852 | A | 12/1990 | Williams ..................... | 250/282 |
| 5,233,190 | A | 8/1993 | Schlereth et al. ............ | 250/291 |
| 6,329,146 | B1 * | 12/2001 | Crooke et al. ................. | 435/6 |
| 6,677,114 | B1 * | 1/2004 | Schneider et al. ............. | 435/4 |
| 6,680,203 | B2 | 1/2004 | Dasseaux ..................... | 436/86 |
| 7,005,255 | B2 | 2/2006 | Kaddurah-Daouk et al. | |
| 2002/0009394 | A1 | 1/2002 | Kostler et al. ................. | 422/65 |
| 2002/0009740 | A1 | 1/2002 | Kaddurah-Daouk et al. | |
| 2002/0019023 | A1 | 2/2002 | Dasseux et al. | |
| 2003/0108876 | A1 | 6/2003 | Speir ............................. | 435/6 |
| 2003/0134304 | A1 | 7/2003 | van der Greef ................ | 435/6 |
| 2004/0029120 | A1 | 2/2004 | Goodenowe | |
| 2004/0146853 | A1 | 7/2004 | Kaddurah-Daouk et al. | |
| 2005/0014132 | A1 | 1/2005 | Kaddurah-Daouk et al. | |
| 2006/0134676 | A1 | 6/2006 | Kaddurah-Daouk et al. | |
| 2006/0134677 | A1 | 6/2006 | Kaddurah-Daouk et al. | |
| 2006/0134678 | A1 | 6/2006 | Kaddurah-Daouk et al. | |
| 2007/0026389 | A1 | 2/2007 | Kaddurah-Daouk et al. | |
| 2007/0072203 | A1 | 3/2007 | Kaddurah-Daouk et al. | |
| 2007/0172820 | A1 | 7/2007 | Kaddurah-Daouk et al. | |
| 2007/0172885 | A1 | 7/2007 | Kaddurah-Daouk et al. | |
| 2007/0178599 | A1 | 8/2007 | Kaddurah-Daouk et al. | |

FOREIGN PATENT DOCUMENTS

| | | |
|---|---|---|
| CA | 2185574 | 3/1995 |
| CA | 2252715 | 4/1997 |
| CA | 2264535 | 8/1997 |
| CA | 2339817 | 8/1999 |
| CA | 2322019 | 9/1999 |
| CA | 2 360 816 | 3/2000 |
| CA | 2303758 | 4/2000 |
| CA | 2303761 | 4/2000 |
| CA | 2370749 | 10/2000 |
| WO | 9823950 A1 | 6/1998 |
| WO | WO 0077712 A | 12/2000 |
| WO | WO01/57519 | 8/2001 |
| WO | 0178652 A2 | 10/2001 |
| WO | WO01/92872 | 12/2001 |
| WO | WO01/96861 | 12/2001 |
| WO | WO 02/04957 A2 | 1/2002 |
| WO | WO 03/005628 A2 | 1/2003 |

OTHER PUBLICATIONS

Trethewey R.N. et al., Current Opinion in Plant Biology, 2:83-85 (1999).
Shinka T. et al., Journal of ChromatographyB: Biomedical Applications, 732:469-477 (1999).
Darius, J., Journal of ChromatographyB: Biomedical Applications, 682:67-72 (1996).
N. Huang et al., J. Am Soc Mass Spectrom 10, 1999, 1166-1173.
R.L. White et al., Analytical Chemistry 55, 1983, 339-343.
E.B.Ledford et al., Analytical Chemistry 52, 1980, 463-468.
Jensen et al., Probing Proteomes Using Capillary Isoelectric Focusing-Electrospray Ionization Fourier Transform Ion Cyclotron Resonance Mass Spectrometry, Anal. Chem., 1999, 2076-2084, vol. 71.

* cited by examiner

Primary Examiner—Carolyn L. Smith
(74) Attorney, Agent, or Firm—Nixon Peabody LLP

(57) ABSTRACT

A method for non-targeted complex sample analysis which involves the following steps. A first step involves providing a data base containing identifying data of known molecules. A second step involves introducing a complex sample containing multiple unidentified molecules into a Fourier Transform Ion Cyclotron Mass Spectrometer to obtain data regarding the molecules in the complex sample. A third step involves comparing the collected data regarding the molecules in the complex sample with the identifying data of known molecules in order to arrive at an identification through comparison of molecules in the sample.

21 Claims, 18 Drawing Sheets

GS-Green Stage; WS-White Stage; TS-Turning Stage; RS-Red Stage

METHOD OF NON-TARGETED COMPLEX SAMPLE ANALYSIS

FIELD OF THE INVENTION

The present invention relates to a method of non-targeted complex sample analysis, with particular application to biology, and genomics in particular.

BACKGROUND OF THE INVENTION

Functional genomics is an emerging field in biotechnology that focuses on the characterization of gene function. All organisms contain only one genotype. However, the expression of this genotype under varying developmental and environmental conditions results in an almost infinite number of possible phenotypes. It is the correlation of gene expression to phenotype that defines functional genomics. To properly study a gene we need to not only know its identity (i.e. sequence) but to be able to observe and characterize its expression patterns in response to developmental and environmental changes, in isolation as well as in relation to the other genes in the genome. To properly study the effects resulting from the expression of a gene we need to be able to characterize the phenotype resulting from this activity in an objective and quantifiable manner. This is what the non-targeted metabolic profiling technology invention described herein enables the functional genomics community to do.

The gene sequences of entire species are now known. Gene-chip technology has made it possible to monitor and quantify the changes in expression of each and every gene within the genome to developmental and environmental changes, simultaneously. Gene-chip technology is, in essence, non-targeted gene expression analysis even though it is, in actuality, a targeted analysis that just so happens to contain all of the possible targets. This is a powerful comprehensive capability, but it was made possible by the fact that the genome is a finite and unitary entity. The analogous phenotypic capability would be to have every metabolite and protein of an organism known and on a chip. This is not possible due to the fact that not only are there multiple phenotypes, but a virtually infinite number of metabolites and proteins are possible. To be complementary to the current state of genomic analysis, phenotypic analysis must be non-targeted in "actuality". The non-targeted metabolic profiling technology described herein is the only platform that satisfies the requirements of non-targeted phenotypic analysis. Furthermore, this technology is not restricted to any one species, but is equally effective in all plant and animal species.

Deciphering the complex molecular makeup of an individual phenotype is a formidable task. To be able to accurately and reproducibly generate this phenotypic information in such a way that the virtually infinite number of possible phenotypes can be compared to one another and correlated to gene expression is the crux of the dilemma that faces functional genomics. On the molecular level, the phenotype of a given biological system can be divided into the proteome and the metabolome. Since gene expression results in protein synthesis, the proteome is the first and most direct link to gene expression. However, due to the complex interactions of metabolic pathways, it is difficult to predict the effects that changes in the expression levels of a given protein will have on the overall cellular processes that it may be involved in. The metabolome, on the other hand, is the summation of all metabolic (proteomic) activities occurring in an organism at any given point in time. The metabolome is therefore a direct measure of the overall or end effect of gene expression on the cellular processes of any given biological system at any given time. For this reason, the metabolome should prove to be the more powerful of the two phenotypes in actually understanding the effects of gene function and manipulation. The non-targeted metabolic profiling technology described herein is the only comprehensive metabolic profiling technology available.

Isolation, identification, and quantitation are the three fundamental requirements of all analytical methods. The primary challenge for a non-targeted metabolome analysis is to meet these requirements for all of the metabolites in the metabolome, simultaneously. The second and perhaps more difficult challenge is to be able to meet these requirements with sufficient throughput and long-term stability such that it can be used side by side with gene-chip technology. Such technology will drastically reduce the time that is required for the function of a particular gene to be elucidated. In addition, databases of such analyses enable very large numbers of phenotypes and genotypes to be objectively and quantitatively compared. There is no such product or technology available to functional genomics scientists at this time. The non-targeted metabolic profiling technology described herein has been extensively tested in multiple species. In all cases, the technology has verified the metabolic variations known to exist between various genotypes and developmental stages of different species.

Key Technology Concept. The non-targeted metabolic profiling technology described herein can separate quantify and identify all of the components in a complex biological sample quickly and simultaneously. This is achieved without any a priori selection of the metabolites of interest and is therefore unbiased. These data are exported to a database that allows the researcher to directly compare one sample to another (i.e. mutant vs. wild-type, flowering vs. stem elongation, drought stress vs. normal growing conditions, etc.) or to organize the entire database by metabolite concentration (i.e. which genotype has the greatest or least expression of a given metabolite). This technology is equally applicable to the study of human disease. To make use of this information, the researcher just types in the empirical formula(s) or the accurate mass(es) of the metabolite(s) he or she is interested in and the software will organize the data accordingly.

The ability to conduct an analysis of the composition of substances in biological samples is critical to many aspects of health care, environmental monitoring as well as the product development process. Typically the amount of a specific substance in a complex mixture is determined by various means. For example, in order to measure analytes in a complex mixture, the analyte(s) of interest must be separated from all of the other molecules in the mixture and then independently measured and identified.

In order to separate the analytes in a complex mixture from one another, unique chemical and/or physical characteristics of each analyte are used by the researcher to resolve the analytes from one another. These unique characteristics are also used to identify the analytes. In all previously published reports of complex mixture analysis, the methodologies require known analytical standards of each potential analyte before the presence and/or identity of a component in the unknown sample can be determined. The analytical standard(s) and the unknown sample(s) are processed in an identical manner through the method and the resulting characteristics of these standards recorded (for example: chromatographic retention time). Using this information, a sample containing unknown components can be analyzed and if a component in the unknown sample displays the same characteristic as one of the known analytical standard (s), the component is postulated to be the same entity as the analytical standard. This is targeted analysis technology. Targeted analysis technology is one-way. The researcher can go from known standard to methodology characteristics but not from methodology characteristics to known standard. The researcher can only confirm or refute the presence and/or amount of one of the previously analyzed standards. The researcher cannot go from the method characteristics of an unknown analyte to its chemical identity. The major drawback of this type of analysis is that any molecule that was not identified prior to analysis is not measured. As a result, much potentially useful information is lost to the researcher. To be truly non-targeted, the method must allow the researcher to equally evaluate all of the components of the mixture, whether they are known or unknown. This is only possible if the defining physical and/or chemical characteristics of the analyte are not related to the method of analysis but are inherent in the composition of the analyte itself (i.e. its atomic composition and therefore its accurate mass).

Key Benefits of Non-Targeted Metabolic Profiling Technology

1. Multidisciplinary. Virtually only one set of analyses would need to be performed on a given sample and the data resulting from this analysis would be available to all scientists regardless of the area of research they are focusing on.
2. Comprehensive. The non-targeted approach assesses ALL metabolite changes and will thus lead to a faster and more accurate determination of gene function/disfunction.
3. Unknown Metabolite Discovery. The non-targeted approach has the potential of identifying key metabolic regulators that are currently unknown, and which would not be monitored in a targeted analysis scenario.
4. High Throughput. The system is can be fully automated and analysis time is short allowing 100's of samples to be analyzed per instrument per day.
5. Quantitative. The system is reproducible and has an effective dynamic range>104. Relative changes in metabolite expression over entire populations can be studied.

Business Impact of Technology. The ability to generate searchable databases of the metabolic profiles of a given organism will represent a revolution in how the effects of genetic manipulation on a species can be studied. Currently our knowledge of the actual genetic code is much greater that our knowledge of the functions of the genes making up this code, After the mapping of the genome, the next greatest challenge will be determining the function and purpose of these gene products and how manipulation of these genes and their expression can be achieved to serve any number of purposes. The time, energy, and cost of investigating the effects of genetic manipulation are great. A database that can be searched for multiple purposes and which contains direct measures of the metabolic profiles of specific genotypes has the potential to dramatically decrease the amount of time required to determine the function of particular gene products. Such a database will reduce the risk of investing a large amount of time and resources researching genes which may have effects on protein expression, but due to down-stream feedback mechanisms, no net effect on metabolism at the whole cell or organism level.

In an article published in CURRENT OPINION IN PLANT BIOLOGY in 1999 entitled "Metabolic Profiling: a Rosetta Stone for genomics?", Trethewey, Krotzky and Willmitzer indicated that exponential developments in computing have opened up the "possibility" of conducting non-targeted experimental science. While recognizing that it would not be possible to work with infinite degrees of freedom, the opinion was advanced that the power of post-experimental data processing would make possible this non-targeted approach. The non-targeted approach described in that article dealt only with the post acquisition analysis of metabolite data; not the non-targeted collection of metabolite data.

Thus the feasibility of non-targeted analysis of complex mixtures is neither obvious nor simple. The three major problems surrounding the non-targeted analysis of complex mixtures are: the ability to separate and identify all of the components in the mixture; the ability to organize the large amounts of data generated from the analysis into a format that can be used for research; and the ability to acquire this data in an automated fashion and in a reasonable amount of time.

SUMMARY OF THE INVENTION

What is required is a method of non-targeted complex sample analysis.

According to the present invention there is provided a method for non-targeted complex sample analysis that involves the following steps. A first step involves providing a database containing identifying data of known molecules (this database contains the elemental compositions of all molecules previously identified in nature, organized by species, metabolic processes, subcellular location, etc.). A second step involves introducing a complex sample containing multiple unidentified molecules into a Fourier Transform Ion Cyclotron Mass Spectrometer to obtain data regarding the molecules in the complex sample. A third step involves comparing the collected data regarding the molecules in the complex sample with the identifying data of known molecules in order to arrive at an identification through comparison of the molecules in the sample. Molecules that are not represented in the database (i.e. unknowns) are automatically identified by determining their empirical formula. Thus, the method allows rapid identification of new molecules within the complex mixture related to specific molecules already identified, as well as identification of those molecules within the complex mixture that bear no relationship to those class or category of molecules already defined. As a result the analysis of complex mixtures is greatly simplified.

The invention, as described, uses the high resolving power of Fourier Transform Ion Cyclotron Mass Spectrometry (FTMS) to separate all of the components within the mixture that have different empirical formulas. This has been shown for petroleum distillates, but not for aqueous biological samples ionized in a "soft" ionization mode, where adduct ions can be problematic. The accurate mass capability of FTMS that enables the determination of empirical formula has been widely established. Furthermore FTMS is capable of performing high resolution/accurate mass 2D MS/MS which provides structural information that can be used to confirm the identities of components that have identical empirical formulas and allows the organization of metabolites based upon common structural components. This capability has been shown by isolated research groups but is not available on a commercial instrument. By integrating these capabilities with an automated sample injection system and an automated data integration and database system, all of the components within a complex mixture can be analyzed rapidly and simultaneously. The data is then exported into a database that can be searched and organized by sample, or analyte. It is to be noted that unlike the approach advocated by Trethewey, Krotzky and Willmitzer, the present method is not dependant upon the advances in post experimental data processing. The non-targeted metabolic profiling technology described herein generates a dataset that is simple and compact. Computing technology capable of organizing and interpreting the described databases is readily available. No new advances are required. Furthermore, the technology does not have the finite limits inherent in the approach of Trethewey, Krotzky and Willmitzer.

BRIEF DESCRIPTION OF THE DRAWINGS

These and other features of the invention will become more apparent from the following description in which reference is made to the appended drawings and figures, the drawings and figures are for the purpose of illustration only and are not intended to in any way limit the scope of the invention to the particular embodiment or embodiments shown, wherein.

DETAILED DESCRIPTION OF THE PREFERRED EMBODIMENT

Figure 1:
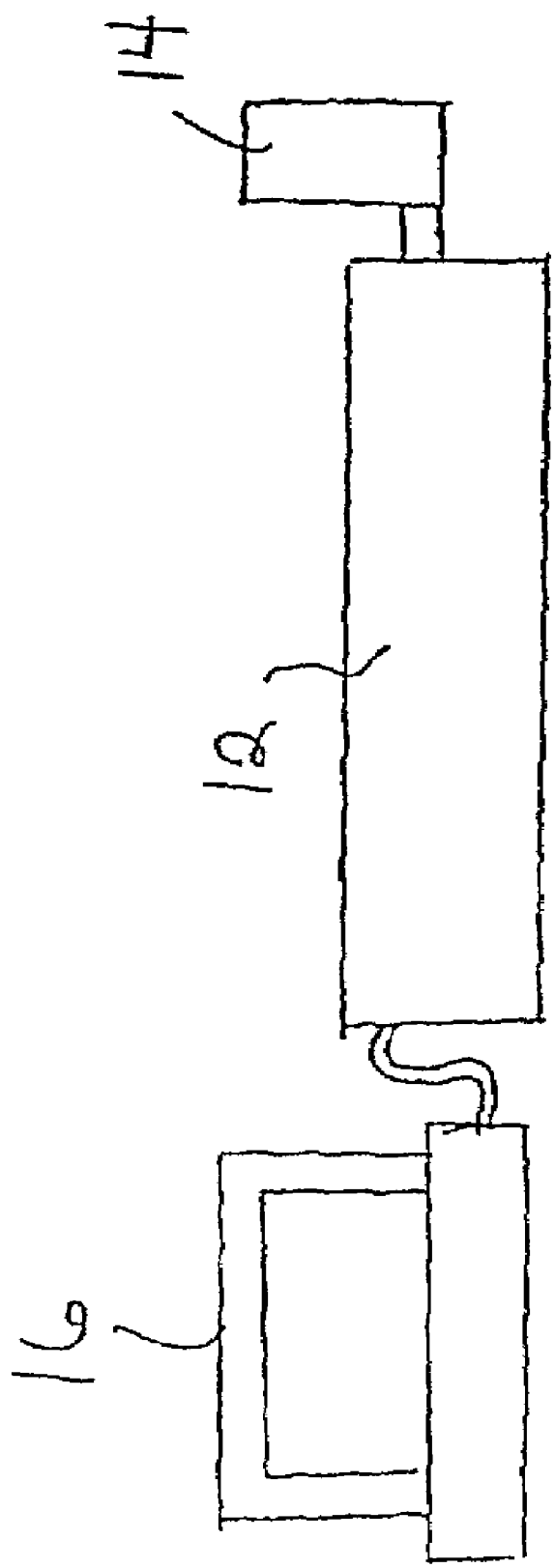
FIG. 1 is a side elevation view depicting non-targeted analysis of complex samples in accordance with the teachings of the present invention.

The preferred method of non-targeted complex sample analysis embodiment will now be described with reference to FIG. 1 The purpose of this invention is to provide a means of analyzing large numbers of complex samples, for example biological extracts, and be able to analyze the information in a non-targeted fashion after the analysis is complete to determine the differences between samples.

In the invention complex samples are directly injected into the FTMS 12 though the use of an autosampler 14 with or without the additional use of a chromatographic column. The components of the mixture are ionized by one of many potential "soft" ionization sources (electrospray, APCI, FAB, SIMS, MALDI, etc.) and then transferred into the ion cyclotron resonance (ICR) cell with or without additional mass-selective pre-separation (quadrupole, hexapole, etc.). The ions are then separated and measured in the ICR cell with or without simultaneous MS/MS occurring The data collected (mass spectrum) is integrated (the mass, relative intensity, absolute intensity of each ion is determined) and processed, with or without calibration with known molecules of known concentrations. These data, with or without isotope elimination and empirical formula calculation, are then transferred to a database 16 that organizes and stores the data for future comparisons and functional analyses. Once stored in the database, individual samples can be compared with one another and those molecules that show different concentrations between the selected samples can be displayed. The entire database can be searched for specific molecules. The samples in the database can be listed from highest to lowest concentration or vice-versa. The molecules detected in the analysis can be compared with a database of known molecules and the molecules automatically identified. For molecules that do not match known molecules, the most likely empirical formulas can be displayed.

This approach provides numerous advantages to the researcher. There is a dramatic increase in the amount of information obtained from each sample (>10× compared to the most comprehensive targeted analysis procedure reported). Information is collected on both known and unknown components of a mixture. There is increased efficiency of data collection (data collection is approximately 10× faster than reported targeted analysis techniques). It provides a basis for unbiased comparison of unknown samples. Effects of gene modification on total cell metabolism can be determined instead of effects on only a small subset of metabolic processes (i.e. the relationship between different metabolic processes can be studied). By analyzing all metabolites the actual step within a metabolic process that is disrupted can be determined. Gene modifications that have an effect on protein expression but no net effect on cell metabolism can be identified. All of these analyses are completed simultaneously in one fast analysis, whereas multiple time-consuming analyses would have to be performed to get identical data at a tremendously higher cost.

Many examples exist for the use of FTMS for the analysis of complex mixtures, but none have introduced the concept of non-targeted analysis followed by database formation. The described method recognizes and utilizes some heretofore unused capabilities in FTMS. FTMS has the theoretical resolving power to separate all of the metabolites of different empirical formula in a complex biological sample. FTMS has the theoretical accurate mass capabilities to assign empirical formulas to all of the metabolites in the complex biological sample. FTMS has the capability to perform 2 dimensional MS/MS on all of the metabolites in a complex biological sample. It is not necessary to know a priori what metabolites are present in a complex biological sample if the analytes could thus be separated and then be identified based upon their empirical formula and MS/MS fragment data and or by comparing them to a database of known analytes. Complex samples can be compared with one another to determine what analytes had different intensities between the samples. A database could be organized by analyte or by common MS/MS fragments. This approach significantly decreases the time and resources needed to elucidate gene function as a result of genetic manipulation, environmental changes, or developmental changes in an organism. One of the many applications of the described method invention include gene function determination in functional genomics research.

Numerous targeted LC-MS methods as well as other screening methods have been developed to analyze specific molecules or groups of molecules in complex samples. The major reason that this invention is novel and not obvious is because it employs a fundamentally different strategy for analytical analysis and is only possible with highly specialized instrumentation and methodology. Although the many independent theoretical research capabilities of FTMS have been known for at least 10 years, FTMS has only been used in a targeted way and for specialized research purposes. In the past 10 years no group has described the application of FTMS employed within the scope of the present invention. The present invention involves the combining of several theoretical FTMS capabilities into a comprehensive, non-targeted metabolic profiling procedure that has commercial utility in the analysis and interpretation of complex mixtures.

The method of the present invention comprises the following steps:

Generation of Known Metabolite Database. The identity (common name and empirical formula) and relevant biological information (species, metabolic processes involved in, cellular and subcellular location, etc) of all known biological metabolites are inputted into a commercial database program (i.e. Microsoft EXCEL, Table I.). The accurate monoisotopic mass of these metabolites is automatically determined along with their [M+H]+ and [M−H]− accurate mass (M+H and M−H refer to the mass of the metabolite when a proton (H+) is either added to the metabolite to create a positively charged ion or removed from the metabolite to create a negatively charged metabolite). The data collected from the FTMS analysis of the complex sample can then be compared to this database to immediately identify many of the components in the complex sample.

Preparation of samples for analysis. The metabolites are extracted from their biological source using any number of extraction/clean-up procedures that are typically used in quantitative analytical chemistry. Procedures are normally tailored to the source of the sample (i.e. leaf tissue, root tissue, blood, urine, brain, etc). For example, a 0.1 g plant leaf sample may be extracted by placing it, 1.0 ml of 50/50 MeOH/0.1% formic acid, and 3 small glass beads in a test tube and then vortexing for one minute to homogenize the sample. The test tube is then centrifuged for 5 minutes. 100 ul of the supernatant is then transferred from the test tube to a 96 well plate. The 96 well plate is placed upon the autosampler. 20 ul of the supernatant is injected into the FTMS.

Typical Operating Conditions

Solvents. 50/50 MeOH/0.1% ammonium hydroxide as the mobile phase and for dilution for all negative ionization analyses and 50/50 MeOH/0.1% formic acid for all positive ion analyses.

Instrumentation. Bruker Daltonics APEX III Fourier Transform Mass Spectrometer (FTMS) equipped with a 7.0 Tesla actively shielded super conducting magnet with electrospray CESI) and atmospheric chemical ionization (APCI) sources. ESI, APCI, and ion transfer conditions were optimized for sensitivity and resolution using a standard mix of serine, tetra-alanine, reserpine, HP Mix, and adrenocorticotrophic hormone fragment 4-10. Instrument conditions were optimized for ion intensity and broadband accumulation over the mass range of 100-1000 amu. One megaword data files were acquired and a sinm data transformation was performed prior to Fourier transform and magnitude calculations.

Calibration. All samples were internally calibrated for mass accuracy over the approximate mass range of 100-1000 amu using a mixture of the above-mentioned standards.

Sample Analysis

Samples are introduced to the FTMS via an autosampler, or in some cases with a syringe pump. When the sample solution reaches the source of the FTMS (the source is where the FTMS ionizes the molecules in the sample solution), then molecules are ionized according to the principles of the particular ionization source used. The source can either be external to the mass analyzer or internal, depending on the type of ionization (for example in ESI and APCI ions are generated external to the mass analyzer and then transferred to the mass analyzer, whereas in electron impact ionization the molecules are ionized internal to the mass analyzer). The ions once generated and transferred (if necessary) to the mass analyzer are then separated and detected in the mass analyzer based upon their mass to charge ratio.

Analyte Detection

All of the analytes within the complex mixture are analyzed simultaneously (see FIGS. 2-5). Structurally specific information (accurate mass with or without accurate MS/MS fragment masses) is obtained for all of the analytes without prior knowledge of the analyte's identity, and then this data is formatted in a way that is amicable to a comprehensive database.

Complex Sample Database Formation

Figure 8:
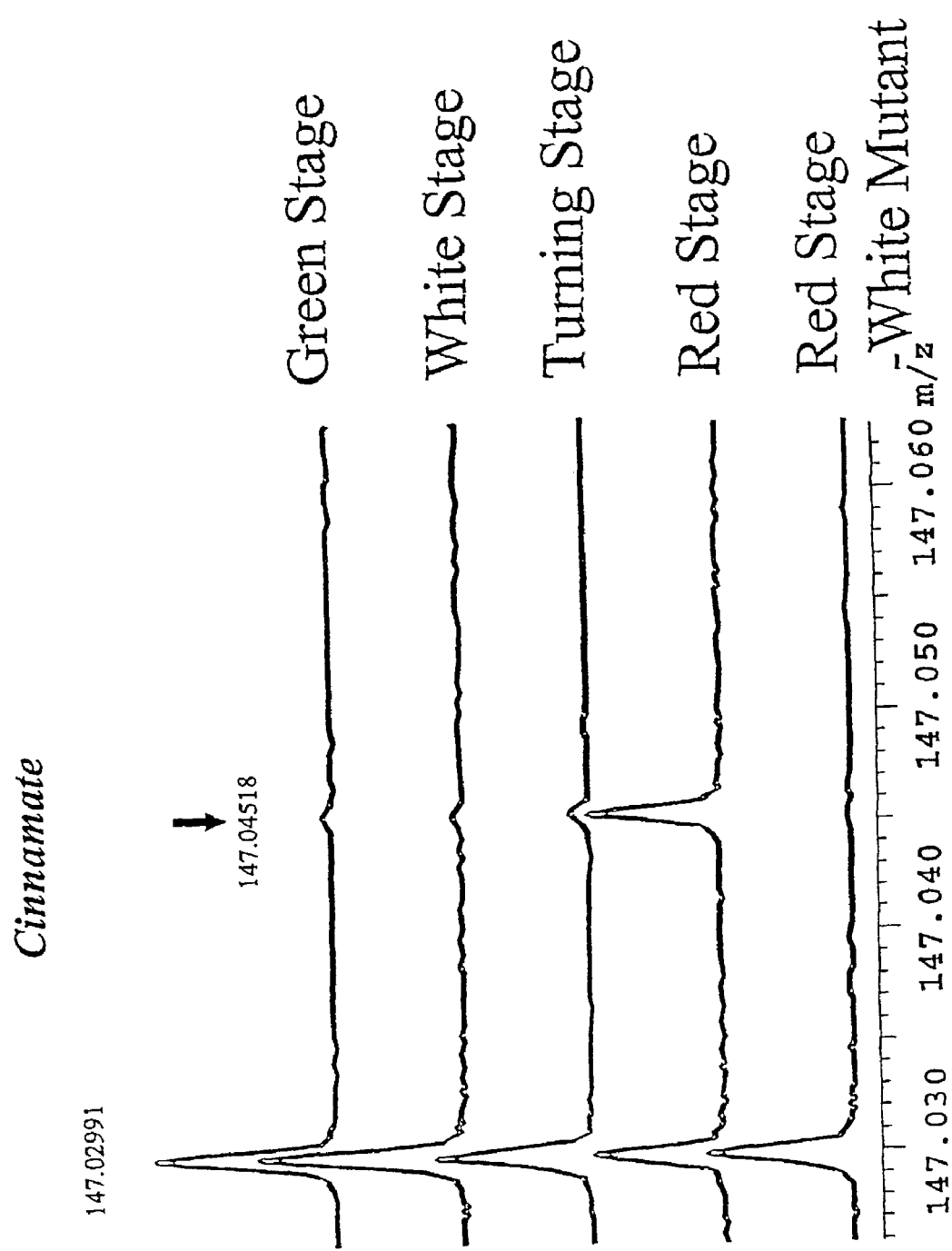
FIG. 8 is an illustration of the extracted mass spectra of Cinnamate from strawberry extracts from different developmental stages.
Figure 9:
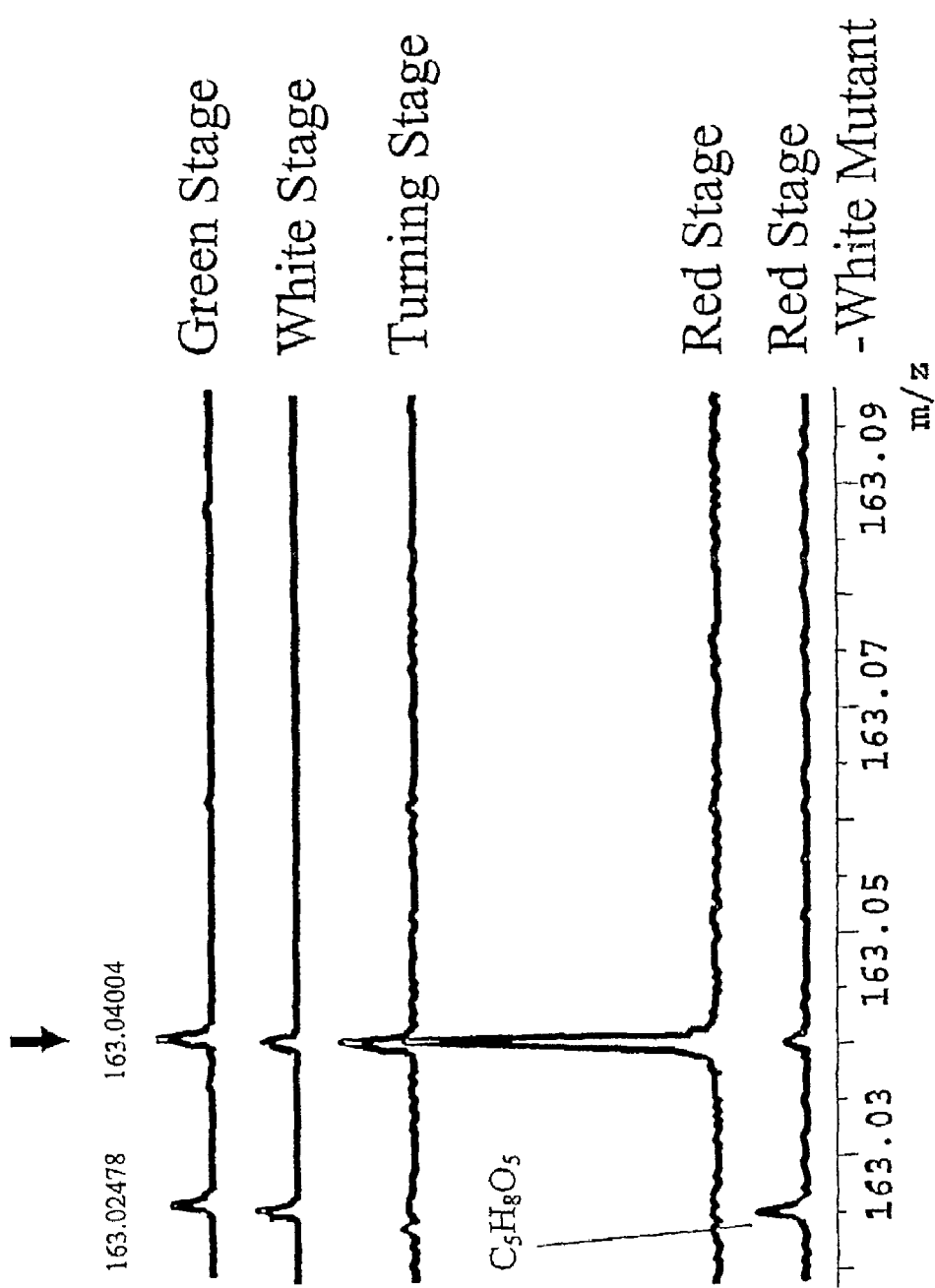
FIG. 9 is an illustration of the extracted mass spectra of 4-Coumarate from strawberry extracts from different developmental stages.
Figure 10:
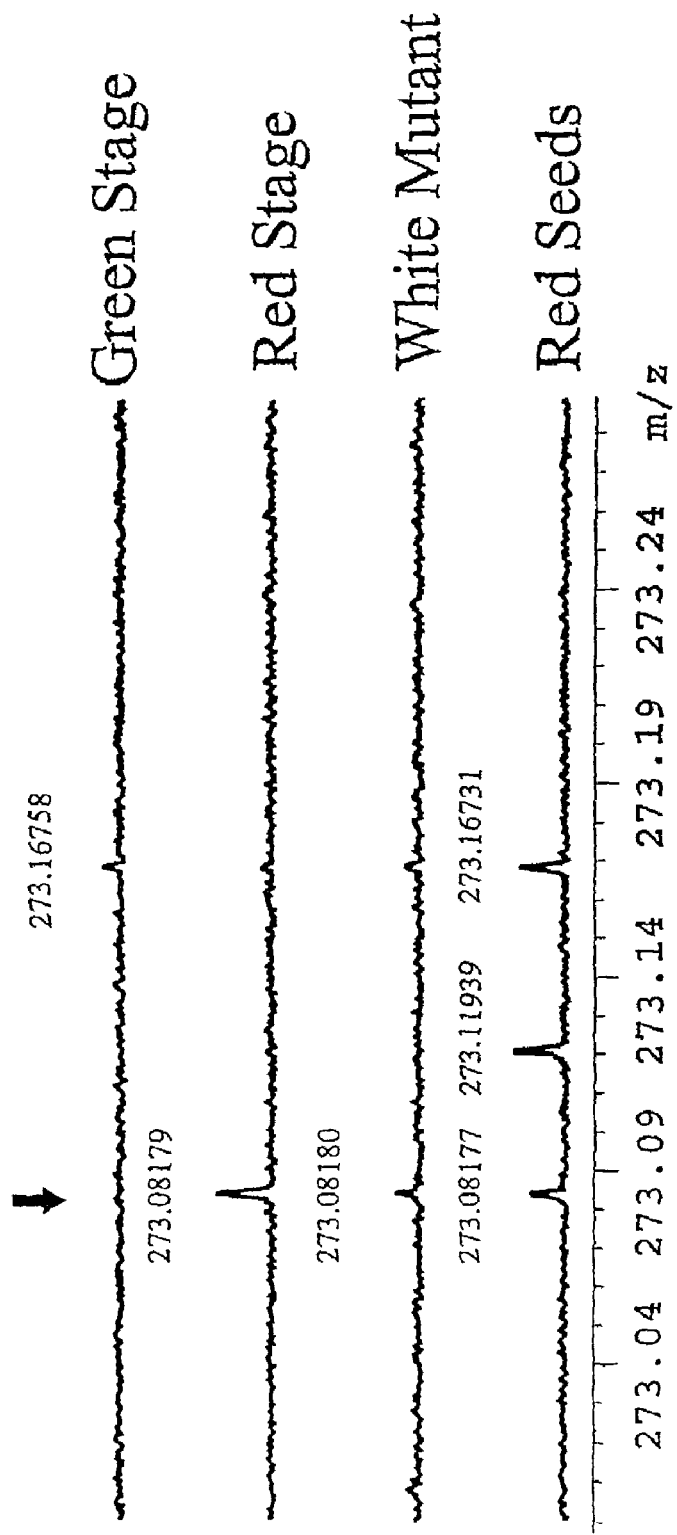
FIG. 10 is an illustration of the extracted mass spectra of Naringenin from strawberry extracts from different developmental stages.
Figure 11:
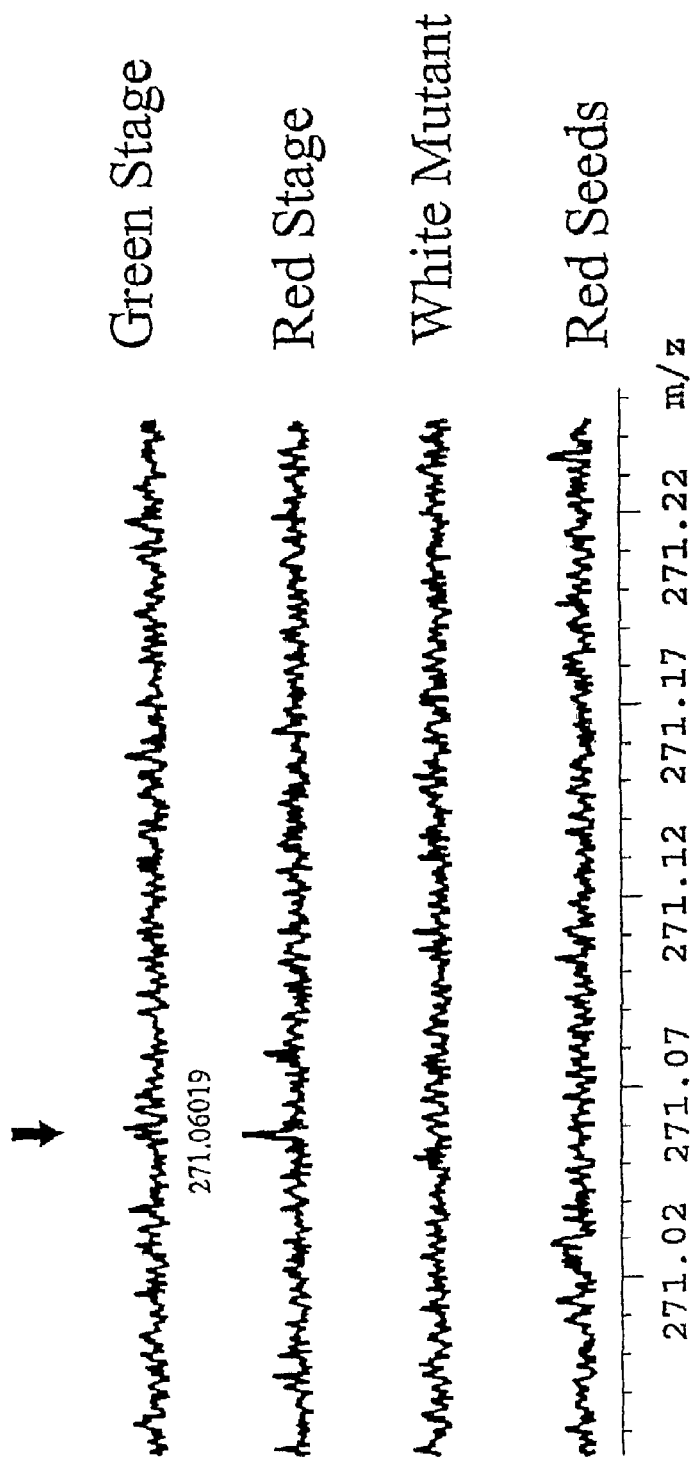
FIG. 11 is an illustration of the extracted mass spectra of Pelargonidin from strawberry extracts from different developmental stages.
Figure 12:
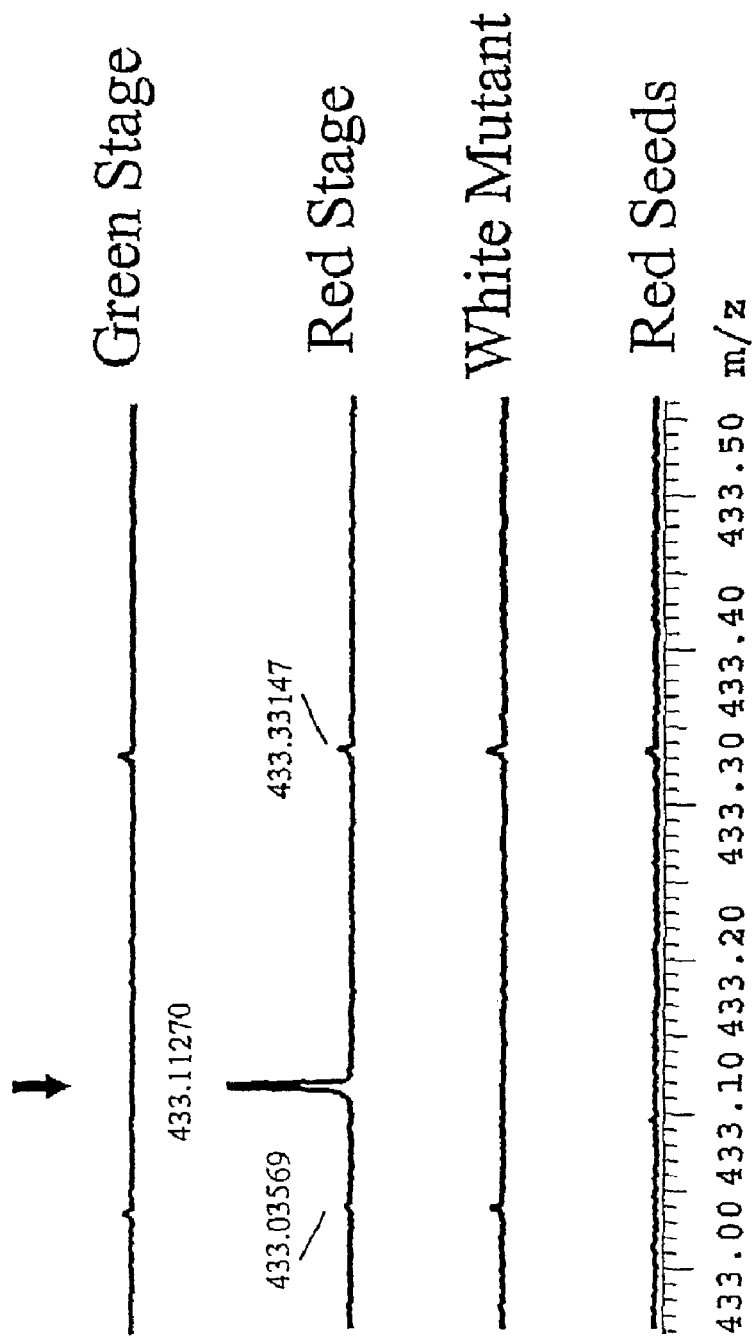
FIG. 12 is an illustration of the extracted mass spectra of Pelargonidin-3-glucoside from strawberry extracts from different developmental stages.

The typical process of database formation involves the following steps:
1. The output of the FTMS (calibrated mass spectrum) is filtered to remove all 13 C isotopes and peaks that have mass defects that do not correspond to singly charged biological metabolites;
2. Each of the peaks in this filtered peak list is then analyzed using the mass analysis program that is part of the instrument manufacturer's software package according to the elemental constraints provided by the researcher. This program ret urns all of the possible elemental compositions that are possible at a given mass within a certain selected error range.
3. Only the data (file name, sample ID, mass, relative intensity, absolute intensity, empirical formula(s)) from those peaks in the filtered peal list that satisfied the above constraints are exported to a final processed data file (Table II). Each sample analysis results in such a final processed data file.
4. Multiple databases can then be formed from the combining and comparing of the data files. Three such databases are:
   a) Direct comparison of two samples to create a database of differences (Table VI);
   b) Combination of multiple files to create a database capable of tracking changes through a series of samples (Table III);
   c) Direct comparison of a whole series of samples to one control sample and then the combination of all the samples in the series into one database to allow comparisons within the series vs a common control (FIG. 8).

The utility of the invention is illustrated in the following examples:

I. The Ability to Compare Different Developmental Stages of an Organism (FIGS. 6-12 Table IV).

Figure 6:
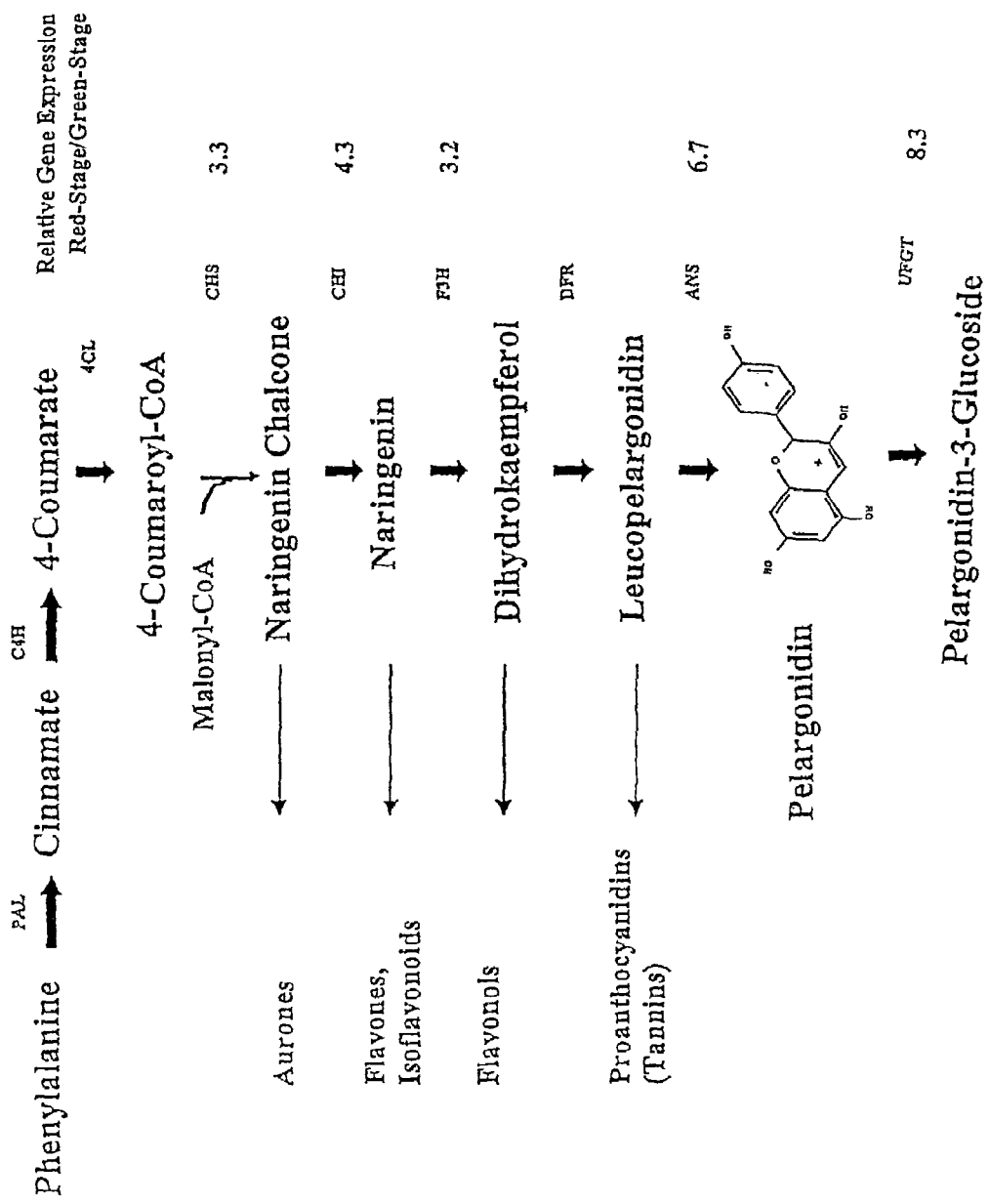
FIG. 6 is an illustration of strawberry pigment pathway (comparison of different developmental stages of an organism).
Figure 7:
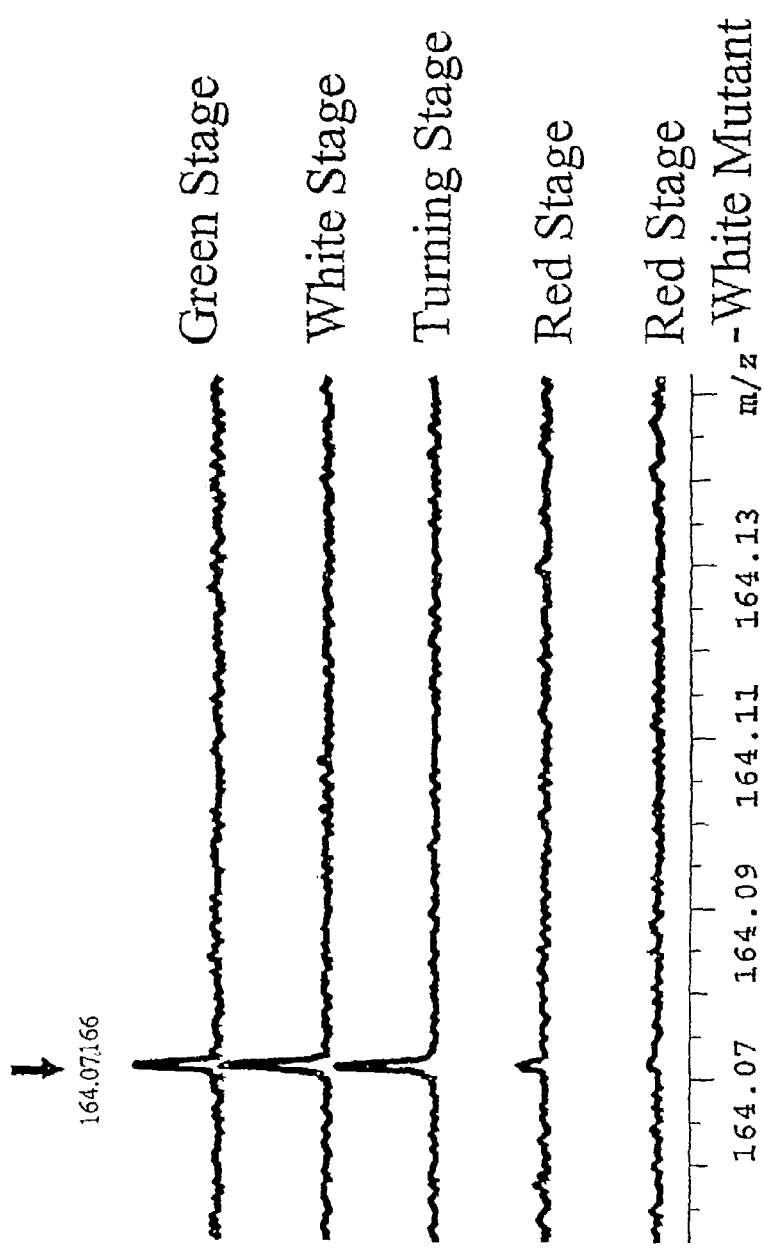
FIG. 7 is an illustration of the extracted mass spectra of Phenylalanine from strawberry extracts from different developmental stages.

In this example, we looked at the strawberry pigment pathway in strawberries. FIG. 6 shows the full metabolic pathway. FIGS. 7-12 show the various metabolites in the pathway that we observed It is to be noted that we were able to look at molecules of vastly different chemical compositions (amino acid, acid, flavenoid, glucoside). Here we were able to see the changes within a single genotype (red strawberry) as a function of developmental stage (green—white—turning—red) and compare it to a different genotype (white mutant). Only the non-targeted metabolic profiling technology described herein has this broad of a spectrum. Furthermore, as indicated in Table IV, these changes in the metabolome are directly correlated with changes in gene expression.

Figure 13:
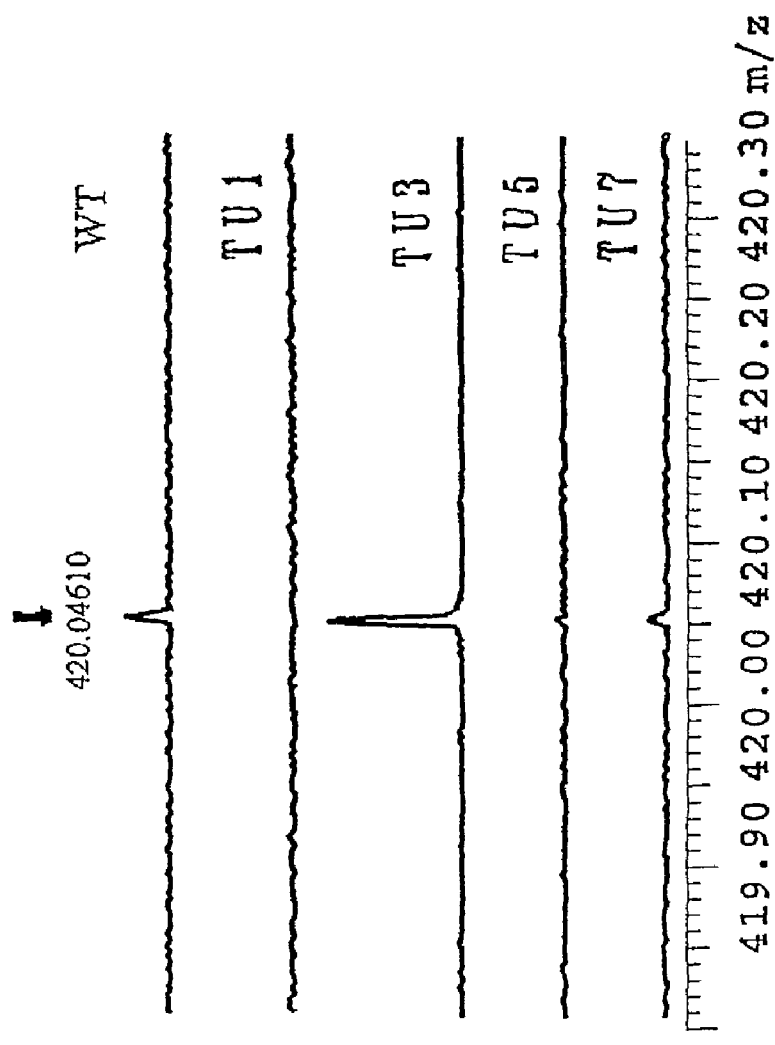
FIG. 13 is an illustration of glucosinolate mutants in *Arabidopsis thaliana* (comparison of genetic mutants to wild-type and identification of unknown metabolites). Relative changes in 3-Methylthiobutyl Glucosinolate illustrated.
Figure 14:
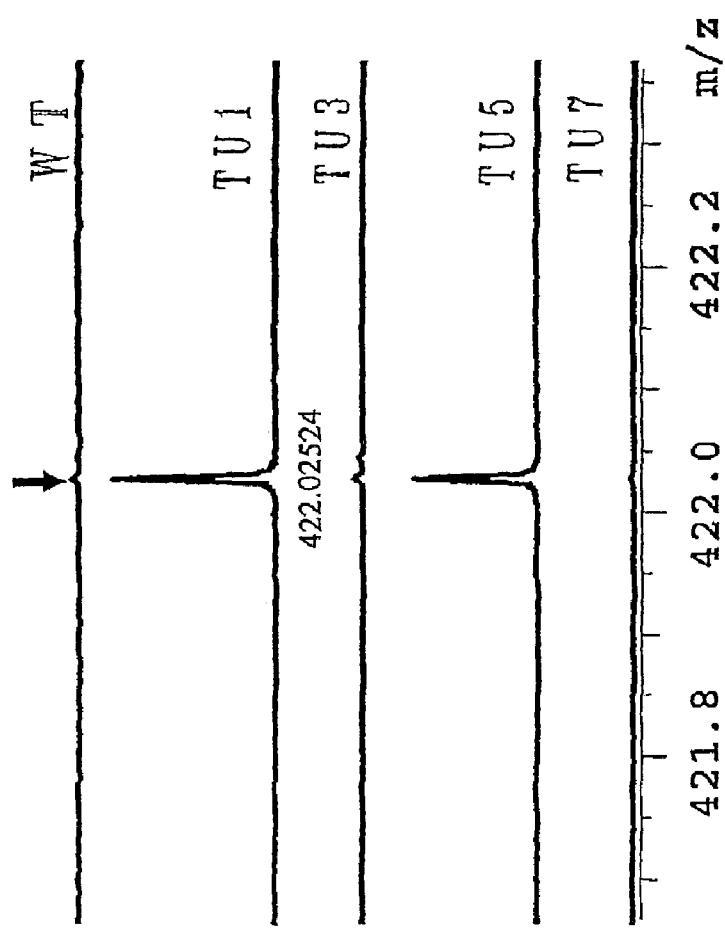
FIG. 14 is an illustration of glucosinolate mutants in *Arabidopsis thaliana* (comparison of genetic mutants to wild-type and identification of unknown metabolites). Relative changes in 3-Methylsulphinylpropyl Glucosinolate illustrated.
Figure 15:
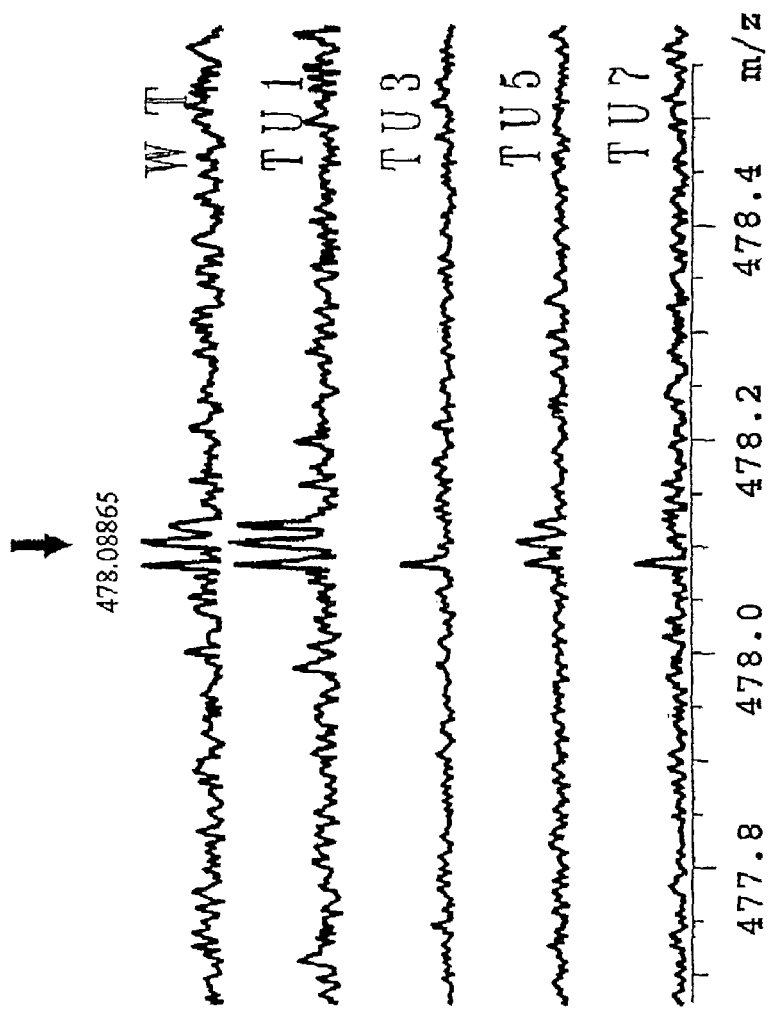
FIG. 15 is an illustration of glucosinolate mutants in *Arabidopsis thaliana* (comparison of genetic mutants to wild-type and identification of unknown metabolites). Relative changes in 3-Methylsulphinylheptyl Glucosinolate illustrated.

II. The Ability to Compare Different Genotypes (FIGS. 13-15. Table V).

In this example three different *Arabidopsis thaliana* mutants (TU1, TU3, TU5) that are known to have changes in the content and concentration of glucosinolates were compared to a wild-type (WT). In this instance the non-targeted metabolic profiling technology described herein was able to confirm previous results as well as identify glucosinolate changes that had never before been observed.

III. The Ability to Detect and Identify Unknown Metabolites Involved in Key Pathways (FIGS. 16 and 17. Table IX).

In this example the flowers of a control (red) tobacco was compared to a white mutant. It was expected that the glucoside (FIG. 16) was the metabolite responsible for color. However, when analyzed by the non-targeted metabolic profiling method, the expected metabolite was not observed, An unknown metabolite (FIG. 17) was detected and identified (Table IX) to be the metabolite responsible for tobacco flower color.

IV. The Ability to Compare the Effects of Different Environmental Conditions on an Organism (Table VI)

In this example the exuate from a carrot root grown under normal growing conditions (sufficient phosphate) was compared to the exuate from a carrot root grown under abnormal growing conditions (insufficient phosphate). Using non-targeted metabolic profiling we were able to identify key plant hormones that are excreted to promote symbiotic fungal growth under conditions of low phosphate.

V. The Ability to Group and Classify Metabolites Based Upon Accurate MS/MS Data (Table VII and Table VIII)

In this example accurate MS/MS fragmentation data was collected on the metabolites that were observed to be increased in the low phosphate conditions described above. Classes of molecules that have a similar substructure can be grouped together (in this case all metabolites with the C10H9N6O2 fragment). This capability greatly enhances the ability to search and characterize different complex mixtures VI. The Ability to Comprehensively Monitor the Metabolites of an Organism (Table X, FIG. 18)

In our study of the developmental stages of strawberry, we characterized the number of metabolites that we were observed as well as the number of metabolites that were observed to have changed in concentration between the different developmental stages. It is the comprehensive nature of this method that allows one to monitor and evaluate virtually all ongoing metabolic processes independently or in relation to one another. No other technology has this capability.

TABLE I

Example of Known Metabolite Database

| Common Name | Metabolic Process | Abbrev. | C | H | N | O | P | S | Monoisotopic Masses | | |
|---|---|---|---|---|---|---|---|---|---|---|---|
| | | | | | | | | | M | M + H | M − H |
| glyoxylate | | | 2 | 2 | | 3 | | | 74.0004 | 75.0076 | 72.9932 |
| Glycine | | Gly, G | 2 | 5 | 1 | 2 | | | 75.0320 | 76.0392 | 74.0248 |
| pyruvic acid | | PA | 3 | 4 | | 3 | | | 88.0160 | 89.0233 | 87.0088 |
| L-Alanine | | Ala, A | 3 | 7 | 1 | 2 | | | 89.0477 | 90.0549 | 88.0404 |
| Lactic Acid | | | 3 | 6 | | 3 | | | 90.0317 | 91.0389 | 89.0245 |
| Cytosine | | | 3 | 5 | 3 | 1 | | | 99.0432 | 100.0505 | 98.0360 |
| Acetoacetic acid | | | 4 | 6 | | 3 | | | 102.0317 | 103.0389 | 101.0245 |
| gamma aminobutyrate | | GABA | 4 | 9 | 1 | 2 | | | 103.0633 | 104.0705 | 102.0561 |

TABLE I-continued

Example of Known Metabolite Database

| Common Name | Metabolic Process | Abbrev. | C | H | N | O | P | S | Monoisotopic Masses | | |
|---|---|---|---|---|---|---|---|---|---|---|---|
| | | | | | | | | | M | M + H | M − H |
| L-serine | | | 3 | 7 | 1 | 3 | | | 105.0426 | 106.0498 | 104.0354 |
| Histamine | | | 5 | 9 | 3 | | | | 111.0796 | 112.0869 | 110.0724 |
| Uracil | | | 4 | 4 | 2 | 2 | | | 112.0273 | 113.0345 | 111.0200 |
| 3-cyanoalanine | | | 4 | 6 | 2 | 2 | | | 114.0429 | 115.0501 | 113.0357 |
| L-Proline | | Pro, P | 5 | 9 | 1 | 2 | | | 115.0633 | 116.0705 | 114.0561 |
| L-Valine | | Val, V | 5 | 11 | 1 | 2 | | | 117.0790 | 118.0862 | 116.0717 |
| succinate | | | 4 | 6 | | 4 | | | 118.0266 | 119.0338 | 117.0194 |
| L-Homoserine | | | 4 | 9 | 1 | 3 | | | 119.0582 | 120.0655 | 118.0510 |
| L-Threonine | | Thr, T | 4 | 9 | 1 | 3 | | | 119.0582 | 120.0655 | 118.0510 |
| phosphoenolpyruvic acid | | PEP | 3 | 6 | | 3 | 1 | | 121.0054 | 122.0127 | 119.9982 |
| L-cysteine | | Cys, C | 3 | 7 | 1 | 2 | | 1 | 121.0197 | 122.0270 | 120.0125 |
| Nicotinic Acid | | | 6 | 5 | 1 | 2 | | | 123.0320 | 124.0392 | 122.0248 |
| Thymine | | | 5 | 6 | 2 | 2 | | | 126.0429 | 127.0501 | 125.0357 |
| L-Isoleucine | | Ile, I | 6 | 13 | 1 | 2 | | | 131.0946 | 132.1018 | 130.0874 |
| L-Leucine | | Leu, L | 6 | 13 | 1 | 2 | | | 131.0946 | 132.1018 | 130.0874 |
| oxaloacetic acid | | OAA | 4 | 4 | | 5 | | | 132.0059 | 133.0131 | 130.9986 |
| L-aspargine | | Asn, N | 4 | 8 | 2 | 3 | | | 132.0535 | 133.0607 | 131.0462 |
| L-Ornithine | | | 5 | 12 | 2 | 2 | | | 132.0899 | 133.0971 | 131.0826 |
| L-Aspartate | | Asp, D | 4 | 7 | 1 | 4 | | | 133.0375 | 134.0447 | 132.0303 |
| Ureidoglycine | | | 3 | 7 | 3 | 3 | | | 133.0487 | 134.0559 | 132.0415 |
| L-malic acid | | | 4 | 6 | | 5 | | | 134.0215 | 135.0287 | 133.0143 |
| Ureidoglycolate | | | 3 | 6 | 2 | 4 | | | 134.0327 | 135.0400 | 133.0255 |
| L-Homocysteine | | | 4 | 9 | 1 | 2 | | 1 | 135.0354 | 136.0426 | 134.0282 |
| Adenine (Vitamin B4) | | | 5 | 5 | 5 | | | | 135.0545 | 136.0617 | 134.0473 |
| Adenine | | | 5 | 5 | 5 | | | | 135.0545 | 136.0617 | 134.0473 |
| 3-Methyleneoxindole | Auxins | | 9 | 7 | 1 | 1 | | | 145.0528 | 146.0600 | 144.0455 |
| Indolealdehyde | Auxins | | 9 | 7 | 1 | 1 | | | 145.0528 | 146.0600 | 144.0455 |
| Indolenine epoxide | Auxins | | 9 | 7 | 1 | 1 | | | 145.0528 | 146.0600 | 144.0455 |
| alpha-Ketoglutarate | | | 5 | 6 | | 5 | | | 146.0215 | 147.0287 | 145.0143 |
| L-Glutamine | | Gln, Q | 5 | 10 | 2 | 3 | | | 146.0691 | 147.0763 | 145.0619 |
| L-Lysine | | Lys, L | 6 | 14 | 2 | 2 | | | 146.1055 | 147.1127 | 145.0983 |
| L-Glutamate | | Glu, E | 5 | 9 | 1 | 4 | | | 147.0531 | 148.0604 | 146.0459 |
| L-Methionine | | Met, M | 5 | 11 | 1 | 2 | | 1 | 149.0510 | 150.0583 | 148.0438 |
| D-ribose | | | 5 | 10 | | 5 | | | 150.0528 | 151.0600 | 149.0456 |
| Guanine | | | 5 | 5 | 5 | 1 | | | 151.0494 | 152.0566 | 150.0422 |
| Indole-3-acetotitrile | Auxins | IAN | 10 | 7 | 2 | | | | 155.0609 | 156.0681 | 154.0537 |

Comments: Any molecule of known chemical composition can be added to the database at any time. The database is comprised of accurate monoisotopic masses. All molecules that have a unique empirical formula will have a unique accurate mass. This mass is a constant and is independent of the methodologies discussed herein making it possible to analyze all of the components in a complex sample in a non-targeted fashion.

Figure 2:
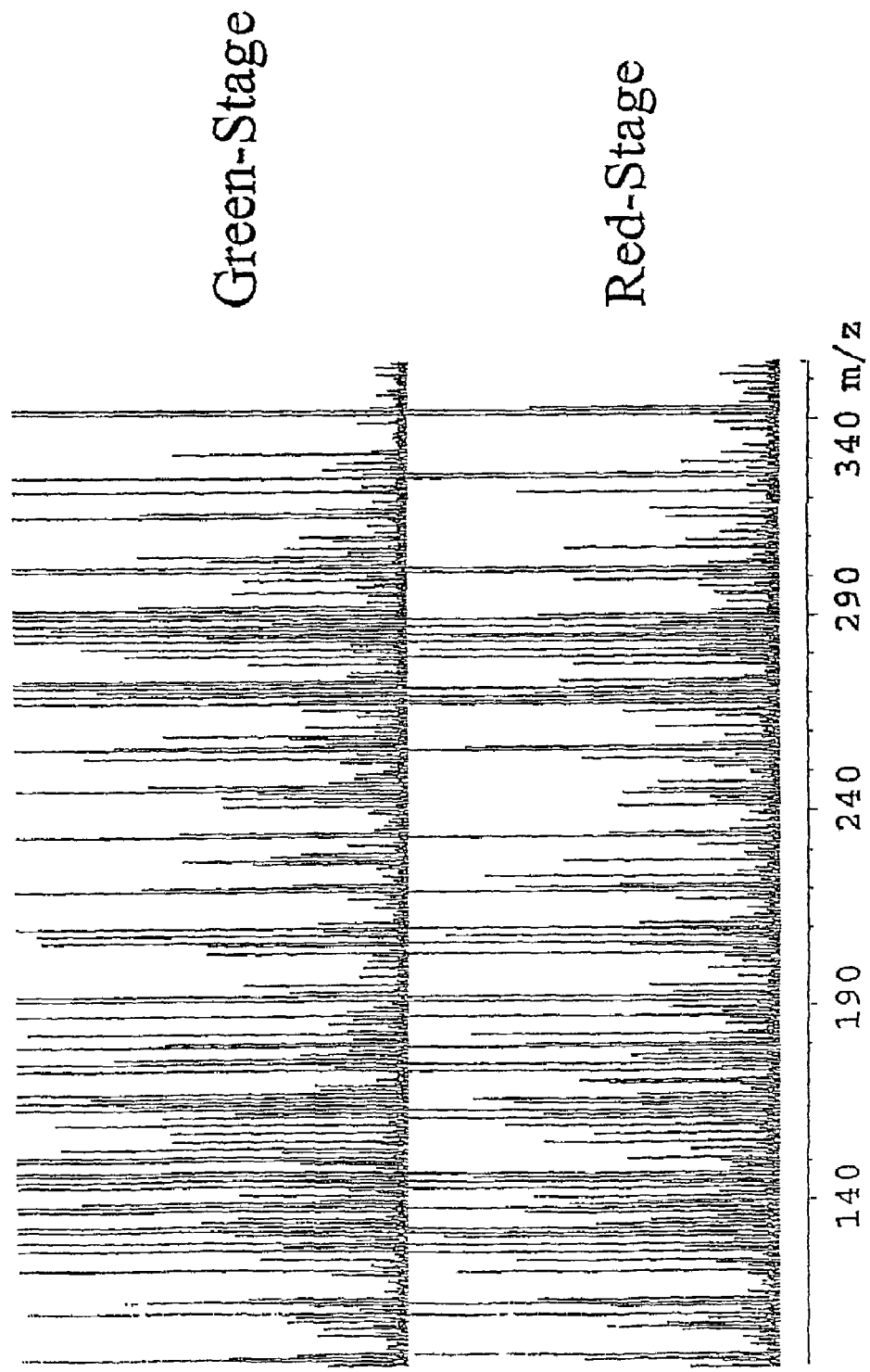
FIG. 2 is an illustration of raw data (mass spectrum) collected from the FTMS showing how the metabolites in the complex mixture are separated from one another. Mass range displayed 100-350 amu.
Figure 3:
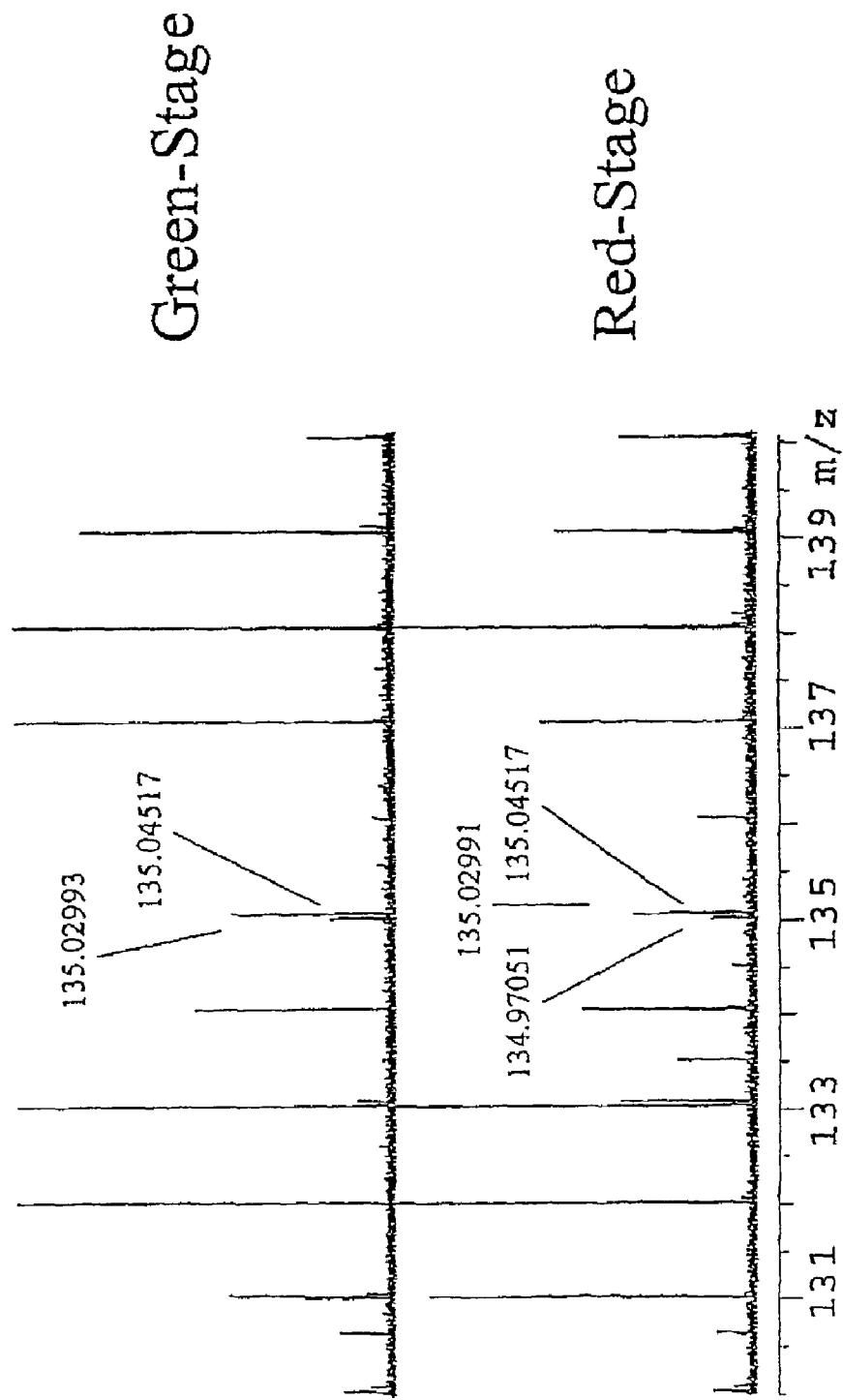
FIG. 3 is an illustration of raw data (mass spectrum) collected from the FTMS showing how the metabolites in the complex mixture are separated from one another. 10 amu mass range displayed.
Figure 4:
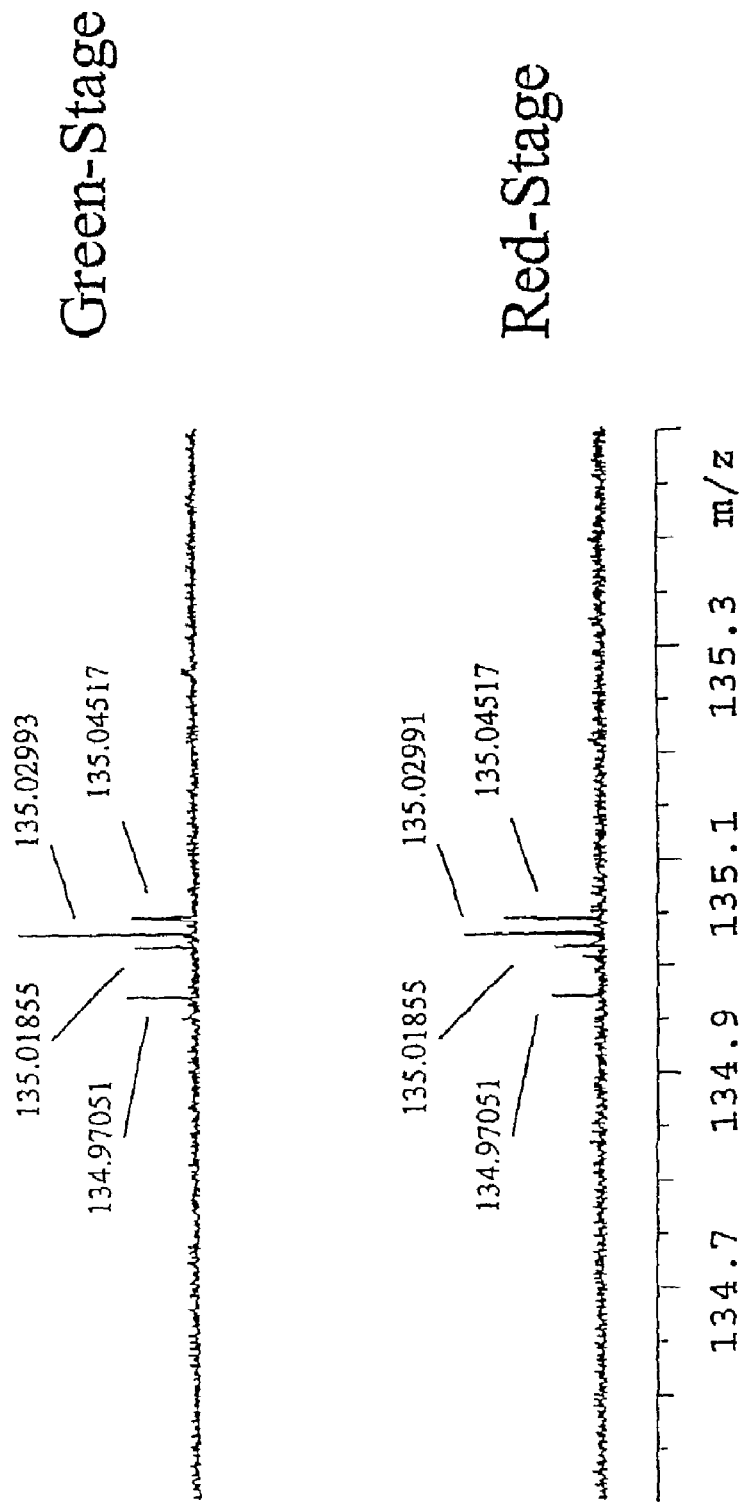
FIG. 4 is an illustration of raw data (mass spectrum) collected from the. FTMS showing how the metabolites in the complex mixture are separated from one another. 1 amu mass range displayed.
Figure 5:
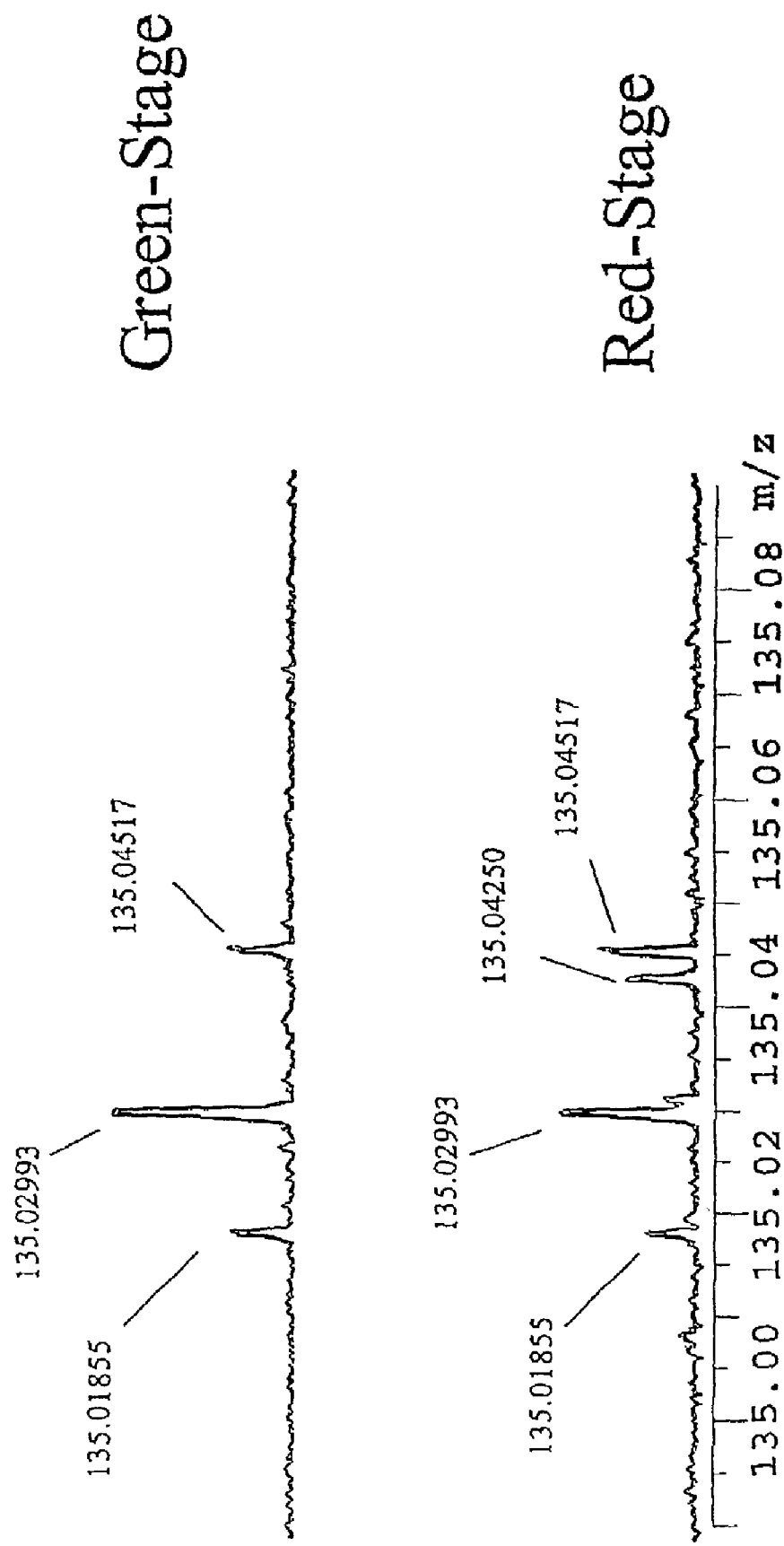
FIG. 5 is an illustration of raw data (mass spectrum) collected from the FTMS showing how the metabolites in the complex mixture are separated from one another. Mass range displayed 100-350 amu. 0.1 amu window.

FIG. 2 shows two raw mass spectrums. The top one is from the extract of a green stage strawberry and the lower one is from the extract of a red stage strawberry. Over 500 unique chemical entities were observed over the mass range displayed above (100-350 amu; which is only a subset of the entire mass range analyzed (100-5000)). FIGS. 3, 4, and 5 show smaller and smaller mass ranges to illustrate the separation of the metabolites.

FIG. 5 shows the resolution of the mass spectrum above 165,000. This extremely high resolution is necessary in order to separate all of the metabolites and thus be able to compare the two samples and determine the changes, if any.

TABLE II

Illustration of processed data (file ID, mass, intensity, empirical formula, relative error)

| FileID | Mass | Int | C | H | N | O | P | S | Err | C | H | N | O | P | S | Err |
|---|---|---|---|---|---|---|---|---|---|---|---|---|---|---|---|---|
| ESI_POS_pri_4_rs2_50_50 | 99.044061 | 2.05E+06 | 5 | 6 | 0 | 2 | 0 | 0 | 0.05 | | | | | | | |
| ESI_POS_pri_3_ts_50_50 | 99.044082 | 1.33E+06 | 5 | 6 | 0 | 2 | 0 | 0 | 0.26 | | | | | | | |
| ESI_POS_pri_3_ts_50_50 | 102.054929 | 2.56E+06 | 4 | 7 | 1 | 2 | 0 | 0 | 0.25 | | | | | | | |
| ESI_POS_pri_1_gs_50_50 | 102.054956 | 3.08E+06 | 4 | 7 | 1 | 2 | 0 | 0 | 0.01 | | | | | | | |
| ESI_POS_pri_2_ws_50_50 | 102.054962 | 1.36E+06 | 4 | 7 | 1 | 2 | 0 | 0 | 0.07 | | | | | | | |
| ESI_POS_pri_4_rs2_50_50 | 104.070595 | 1.93E+06 | 4 | 9 | 1 | 2 | 0 | 0 | 0.10 | | | | | | | |
| ESI_POS_pri_4_rs1_50_50 | 104.070624 | 1.75E+06 | 4 | 9 | 1 | 2 | 0 | 0 | 0.18 | | | | | | | |
| ESI_POS_pri_5_gs_acn | 104.106977 | 2.73E+06 | 5 | 13 | 1 | 1 | 0 | 0 | 0.13 | | | | | | | |
| ESI_POS_pri_2_ws_50_50 | 104.106979 | 2.73E+06 | 5 | 13 | 1 | 1 | 0 | 0 | 0.11 | | | | | | | |
| ESI_POS_pri_6_ws_acn | 104.106981 | 1.84E+06 | 5 | 13 | 1 | 1 | 0 | 0 | 0.09 | | | | | | | |
| ESI_POS_pri_1_gs_50_50 | 104.107 | 3.88E+06 | 5 | 13 | 1 | 1 | 0 | 0 | 0.09 | | | | | | | |
| ESI_POS_pri_3_ts_50_50 | 106.049869 | 1.21E+08 | 3 | 7 | 1 | 3 | 0 | 0 | 0.01 | | | | | | | |
| ESI_POS_pri_1_gs_50_50 | 106.04987 | 1.36E+08 | 3 | 7 | 1 | 3 | 0 | 0 | 0.00 | | | | | | | |

TABLE II-continued

Illustration of processed data (file ID, mass, intensity, empirical formula, relative error)

| FileID | Mass | Int | C | H | N | O | P | S | Err | C | H | N | O | P | S | Err |
|---|---|---|---|---|---|---|---|---|---|---|---|---|---|---|---|---|
| ESI_POS_pri_2_ws_50_50 | 106.04987 | 1.63E+08 | 3 | 7 | 1 | 3 | 0 | 0 | 0.00 | | | | | | | |
| ESI_POS_pri_4_rs1_50_50 | 106.04987 | 1.08E+08 | 3 | 7 | 1 | 3 | 0 | 0 | 0.00 | | | | | | | |
| ESI_POS_pri_4_rs2_50_50 | 106.04987 | 1.53E+08 | 3 | 7 | 1 | 3 | 0 | 0 | 0.00 | | | | | | | |
| ESI_POS_pri_5_gs_acn | 106.04987 | 2.59E+08 | 3 | 7 | 1 | 3 | 0 | 0 | 0.00 | | | | | | | |
| ESI_POS_pri_6_ws_acn | 106.04987 | 2.45E+08 | 3 | 7 | 1 | 3 | 0 | 0 | 0.00 | | | | | | | |
| ESI_POS_pri_7_ts_acn | 106.04987 | 2.62E+08 | 3 | 7 | 1 | 3 | 0 | 0 | 0.00 | | | | | | | |
| ESI_POS_pri_8_rs1_acn | 106.04987 | 2.48E+08 | 3 | 7 | 1 | 3 | 0 | 0 | 0.00 | | | | | | | |
| ESI_POS_pri_8_rs2_acn | 106.04987 | 2.33E+08 | 3 | 7 | 1 | 3 | 0 | 0 | 0.00 | | | | | | | |
| ESI_POS_pri_6_ws_acn | 107.070237 | 1.34E+06 | 4 | 10 | 0 | 3 | 0 | 0 | 0.31 | | | | | | | |
| ESI_POS_pri_8_rs1_acn | 107.070322 | 1.28E+06 | 4 | 10 | 0 | 3 | 0 | 0 | 0.48 | | | | | | | |
| ESI_POS_pri_7_ts_acn | 108.080743 | 2.79E+06 | 7 | 9 | 1 | 0 | 0 | 0 | 0.30 | | | | | | | |
| ESI_POS_pri_4_rs2_50_50 | 109.028414 | 1.65E+06 | 6 | 4 | 0 | 2 | 0 | 0 | 0.07 | | | | | | | |
| ESI_POS_pri_4_rs2_50_50 | 111.044016 | 1.41E+06 | 6 | 6 | 0 | 2 | 0 | 0 | 0.36 | | | | | | | |
| ESI_POS_pri_8_rs2_acn | 114.091316 | 2.74E+06 | 6 | 11 | 1 | 1 | 0 | 0 | 0.21 | | | | | | | |
| ESI_POS_pri_1_gs_50_50 | 114.091319 | 3.02E+06 | 6 | 11 | 1 | 1 | 0 | 0 | 0.19 | | | | | | | |
| ESI_POS_pri_4_rs1_50_50 | 114.091336 | 1.76E+06 | 6 | 11 | 1 | 1 | 0 | 0 | 0.04 | | | | | | | |
| ESI_POS_pri_5_gs_acn | 114.091337 | 3.87E+06 | 6 | 11 | 1 | 1 | 0 | 0 | 0.03 | | | | | | | |
| ESI_POS_pri_2_ws_50_50 | 114.091342 | 2.70E+06 | 6 | 11 | 1 | 1 | 0 | 0 | 0.01 | | | | | | | |
| ESI_POS_pri_7_ts_acn | 114.091346 | 3.26E+06 | 6 | 11 | 1 | 1 | 0 | 0 | 0.05 | | | | | | | |
| ESI_POS_pri_6_ws_acn | 114.091358 | 3.18E+06 | 6 | 11 | 1 | 1 | 0 | 0 | 0.15 | | | | | | | |
| ESI_POS_pri_8_rs1_acn | 114.091375 | 2.74E+06 | 6 | 11 | 1 | 1 | 0 | 0 | 0.30 | | | | | | | |
| ESI_POS_pri_4_rs2_50_50 | 114.091377 | 2.53E+06 | 6 | 11 | 1 | 1 | 0 | 0 | 0.32 | | | | | | | |
| ESI_POS_pri_3_ts_50_50 | 114.091404 | 2.21E+06 | 6 | 11 | 1 | 1 | 0 | 0 | 0.56 | | | | | | | |
| ESI_POS_pri_4_rs2_50_50 | 115.038958 | 3.43E+06 | 5 | 6 | 0 | 3 | 0 | 0 | 0.11 | | | | | | | |
| ESI_POS_pri_5_gs_acn | 115.038978 | 2.03E+06 | 5 | 6 | 0 | 3 | 0 | 0 | 0.07 | | | | | | | |
| ESI_POS_pri_2_ws_50_50 | 115.038984 | 1.84E+06 | 5 | 6 | 0 | 3 | 0 | 0 | 0.12 | | | | | | | |
| ESI_POS_pri_8_rs1_acn | 115.038999 | 1.57E+06 | 5 | 6 | 0 | 3 | 0 | 0 | 0.25 | | | | | | | |
| ESI_POS_pri_4_rs1_50_50 | 115.039032 | 1.86E+06 | 5 | 6 | 0 | 3 | 0 | 0 | 0.53 | | | | | | | |
| ESI_POS_pri_3_ts_50_50 | 115.03905 | 1.67E+06 | 5 | 6 | 0 | 3 | 0 | 0 | 0.69 | | | | | | | |
| ESI_POS_pri_2_ws_50_50 | 116.034226 | 1.76E+06 | 4 | 5 | 1 | 3 | 0 | 0 | 0.06 | | | | | | | |
| ESI_POS_pri_1_gs_50_50 | 116.034233 | 2.43E+06 | 4 | 5 | 1 | 3 | 0 | 0 | 0.12 | | | | | | | |
| ESI_POS_pri_3_ts_50_50 | 116.03425 | 2.07E+06 | 4 | 5 | 1 | 3 | 0 | 0 | 0.26 | | | | | | | |
| ESI_POS_pri_1_gs_50_50 | 116.070538 | 2.60E+06 | 5 | 9 | 1 | 2 | 0 | 0 | 0.58 | | | | | | | |
| ESI_POS_pri_3_ts_50_50 | 116.070601 | 1.46E+06 | 5 | 9 | 1 | 2 | 0 | 0 | 0.03 | | | | | | | |
| ESI_POS_pri_2_ws_50_50 | 116.070643 | 1.46E+06 | 5 | 9 | 1 | 2 | 0 | 0 | 0.33 | | | | | | | |
| ESI_POS_pri_4_rs1_50_50 | 118.086184 | 1.56E+06 | 5 | 11 | 1 | 2 | 0 | 0 | 0.60 | | | | | | | |
| ESI_POS_pri_1_gs_50_50 | 118.086217 | 4.10E+06 | 5 | 11 | 1 | 2 | 0 | 0 | 0.32 | | | | | | | |
| ESI_POS_pri_4_rs2_50_50 | 118.086231 | 1.52E+06 | 5 | 11 | 1 | 2 | 0 | 0 | 0.20 | | | | | | | |
| ESI_POS_pri_2_ws_50_50 | 118.086234 | 1.23E+06 | 5 | 11 | 1 | 2 | 0 | 0 | 0.18 | | | | | | | |
| ESI_POS_pri_3_ts_50_50 | 118.086246 | 2.74E+06 | 5 | 11 | 1 | 2 | 0 | 0 | 0.08 | | | | | | | |
| ESI_POS_pri_5_gs_acn | 118.086249 | 2.53E+06 | 5 | 11 | 1 | 2 | 0 | 0 | 0.05 | | | | | | | |

Comments: The mass spectrum is processed such that the 13C isotopes are first eliminated (this is only possible in FTMS analysis due to the high resolution and mass accuracy).

Then the remaining peaks are automatically analyzed using the mass analysis program that is included with the instrument using specific constraints chosen by the researcher (in the above example only those peaks that have the appropriate combination of carbon (C), hydrogen (H), oxygen (O), nitrogen (N), sulfur (S), or phosphorus (P) are returned). The final dataset now only contains monoisotopic, singly charged metabolites that have an accuracy of measurement of less than 1 ppm (err).

TABLE III

Illustration of the database generated from the processed data;

| Empirical Formula | | | | | | Green Stage | | White Stage | | | Turning Stage | | | |
|---|---|---|---|---|---|---|---|---|---|---|---|---|---|---|
| C | H | N | O | P | S | Mass | Int | Mass | Int | WS/GS | Mass | Int | TS/GS | TS/WS |
| 21 | 20 | 0 | 10 | 0 | 0 | nf | 1.30E+06 | nf | 1.30E+06 | 100 | 433.1130 | 1.68E+07 | 1292 | 1292 |
| 25 | 34 | 6 | 19 | 0 | 0 | nf | 1.30E+06 | 723.1955 | 5.21E+07 | 4008 | 723.1952 | 1.12E+08 | 8615 | 215 |
| 24 | 22 | 0 | 13 | 0 | 0 | nf | 1.30E+06 | nf | 1.30E+06 | 100 | 519.1132 | 3.16E+06 | 243 | 243 |
| 22 | 32 | 6 | 1 | 0 | 0 | nf | 1.30E+06 | nf | 1.30E+06 | 100 | nf | 1.30E+06 | 100 | 100 |
| 46 | 35 | 11 | 1 | 0 | 1 | nf | 1.30E+06 | 790.2821 | 2.62E+07 | 2015 | 790.2819 | 5.71E+07 | 4392 | 218 |
| 19 | 17 | 11 | 3 | 0 | 0 | nf | 1.30E+06 | 448.1592 | 3.53E+06 | 2715 | 448.1591 | 4.88E+07 | 3754 | 138 |
| 11 | 16 | 4 | 9 | 0 | 1 | nf | 1.30E+06 | 381.0710 | 1.68E+07 | 1292 | 381.0710 | 2.19E+07 | 1685 | 130 |
| 9 | 18 | 8 | 5 | 0 | 3 | nf | 1.30E+06 | nf | 1.30E+06 | 100 | nf | 1.30E+06 | 100 | 100 |
| 30 | 67 | 19 | 4 | 0 | 0 | nf | 1.30E+06 | nf | 1.30E+06 | 100 | 758.5697 | 3.27E+07 | 2515 | 2515 |

TABLE III-continued

Illustration of the database generated from the processed data;

| 47 | 71 | 7 | 3 | 0 | 0 | nf | 1.30E+06 | 782.5697 | 3.67E+07 | 2823 | 782.5694 | 3.19E+07 | 2454 | 87 |
|---|---|---|---|---|---|---|---|---|---|---|---|---|---|---|
| 22 | 40 | 14 | 5 | 0 | 2 | nf | 1.30E+06 | 645.2825 | 2.27E+07 | 1746 | 645.2823 | 2.71E+07 | 2085 | 119 |
| 23 | 24 | 8 | 5 | 0 | 1 | nf | 1.30E+06 | 525.1667 | 4.15E+06 | 319 | 525.1663 | 1.54E+07 | 1185 | 371 |
| 9 | 16 | 8 | 1 | 0 | 3 | nf | 1.30E+06 | nf | 1.30E+06 | 100 | 349.0683 | 1.42E+06 | 109 | 109 |
| 20 | 28 | 4 | 11 | 0 | 1 | nf | 1.30E+06 | 533.1550 | 5.75E+06 | 442 | 533.1551 | 1.54E+07 | 1185 | 268 |
| 22 | 29 | 3 | 1 | 0 | 3 | nf | 1.30E+06 | 448.1546 | 1.34E+07 | 1031 | 448.1545 | 1.73E+07 | 1331 | 129 |
| 33 | 54 | 6 | 9 | 0 | 0 | nf | 1.30E+06 | 679.4031 | 1.52E+07 | 1169 | 679.4025 | 1.58E+07 | 1215 | 104 |
| 14 | 29 | 3 | 13 | 0 | 0 | nf | 1.30E+06 | 448.1774 | 1.17E+07 | 900 | 448.1774 | 1.53E+07 | 1177 | 131 |
| 15 | 20 | 0 | 11 | 0 | 0 | nf | 1.30E+06 | nf | 1.30E+06 | 100 | nf | 1.30E+06 | 100 | 100 |
| 21 | 12 | 0 | 2 | 0 | 1 | nf | 1.30E+06 | nf | 1.30E+06 | 100 | nf | 1.30E+06 | 100 | 100 |
| 40 | 34 | 8 | 0 | 0 | 3 | nf | 1.30E+06 | nf | 1.30E+06 | 100 | nf | 1.30E+06 | 100 | 100 |
| 27 | 50 | 2 | 5 | 0 | 2 | nf | 1.30E+06 | 547.3240 | 1.21E+07 | 931 | 547.3239 | 1.22E+07 | 938 | 101 |
| 21 | 44 | 2 | 21 | 0 | 2 | nf | 1.30E+06 | nf | 1.30E+06 | 100 | nf | 1.30E+06 | 100 | 100 |
| 30 | 42 | 0 | 17 | 0 | 1 | 707.222203 | 5.04E+06 | 707.2220 | 1.94E+07 | 385 | 707.2216 | 5.34E+07 | 1060 | 275 |
| 12 | 24 | 4 | 11 | 0 | 1 | nf | 1.30E+06 | nf | 1.30E+06 | 100 | nf | 1.30E+06 | 100 | 100 |

| Empirical Formula | | | | | | Red Stage | | | | |
|---|---|---|---|---|---|---|---|---|---|---|
| C | H | N | O | P | S | Mass | Int | RS1/GS | RS/WS | RS/TS |
| 21 | 20 | 0 | 10 | 0 | 0 | 433.1128 | 2.98E+08 | 22923 | 22923 | 1774 |
| 25 | 34 | 6 | 19 | 0 | 0 | 723.1953 | 1.41E+08 | 10846 | 271 | 126 |
| 24 | 22 | 0 | 13 | 0 | 0 | 519.1133 | 1.21E+08 | 9308 | 9308 | 3829 |
| 22 | 32 | 6 | 1 | 0 | 0 | 397.2714 | 6.32E+07 | 4862 | 4862 | 4862 |
| 46 | 35 | 11 | 1 | 0 | 1 | 790.2822 | 4.54E+07 | 3492 | 173 | 80 |
| 19 | 17 | 11 | 3 | 0 | 0 | 448.1592 | 4.02E+07 | 3092 | 114 | 82 |
| 11 | 16 | 4 | 9 | 0 | 1 | 381.0709 | 2.75E+07 | 2115 | 164 | 126 |
| 9 | 18 | 8 | 5 | 0 | 3 | 415.0638 | 2.69E+07 | 2069 | 2069 | 2069 |
| 30 | 67 | 19 | 4 | 0 | 0 | 758.5698 | 2.44E+07 | 1877 | 1877 | 75 |
| 47 | 71 | 7 | 3 | 0 | 0 | 782.5697 | 2.12E+07 | 1631 | 58 | 66 |
| 22 | 40 | 14 | 5 | 0 | 2 | 645.2825 | 2.12E+07 | 1631 | 93 | 78 |
| 23 | 24 | 8 | 5 | 0 | 1 | 525.1664 | 1.52E+07 | 1169 | 366 | 99 |
| 9 | 16 | 8 | 1 | 0 | 3 | 349.0685 | 1.50E+07 | 1154 | 1154 | 1056 |
| 20 | 28 | 4 | 11 | 0 | 1 | 533.1550 | 1.38E+07 | 1062 | 240 | 90 |
| 22 | 29 | 3 | 1 | 0 | 3 | 448.1546 | 1.32E+07 | 1015 | 99 | 76 |
| 33 | 54 | 6 | 9 | 0 | 0 | 679.4028 | 1.31E+07 | 1008 | 86 | 83 |
| 14 | 29 | 3 | 13 | 0 | 0 | 448.1774 | 1.28E+07 | 985 | 109 | 84 |
| 15 | 20 | 0 | 11 | 0 | 0 | 377.1078 | 1.24E+07 | 954 | 954 | 954 |
| 21 | 12 | 0 | 2 | 0 | 1 | 329.0634 | 1.17E+07 | 900 | 900 | 900 |
| 40 | 34 | 8 | 0 | 0 | 3 | 723.2143 | 1.13E+07 | 869 | 869 | 869 |
| 27 | 50 | 2 | 5 | 0 | 2 | 547.3240 | 1.06E+07 | 815 | 88 | 87 |
| 21 | 44 | 2 | 21 | 0 | 2 | 725.1951 | 1.05E+07 | 808 | 808 | 808 |
| 30 | 42 | 0 | 17 | 0 | 1 | 707.2218 | 3.99E+07 | 792 | 206 | 75 |
| 12 | 24 | 4 | 11 | 0 | 1 | 433.1235 | 9.92E+06 | 763 | 763 | 763 |

Comments: In Table III, the data was sorted according to the relative expression of metabolites in the red stage vs the green stage of strawberry. The data can be organized by any field. What is observed is that the metabolite C10H20O10 has a concentration that is at least 22923% of that observed in the green stage (this metabolite is not observed in the green stage so the value is a % of the background noise). This metabolite can be identified by its empirical formula as pelargonidin-3-glucoside, the primary pigment observed in strawberries that give them their red color. This process is automated.

TABLE IV

Comparison of Metabolite and Gene Expression Data in Strawberry Color Formation (Red Stage vs. Green Stage)

| Metabolic Pathway | Relative Metabolite Expression | Relative Gene Expression |
|---|---|---|
| 4-Coumarate-COA to Naringenin Chalcone | 4.3 | 3.3 |
| Naringenin Chalcone to Naringenin | 4.3 | 4.3 |
| Leucopelargonidin to Pelargonidin | 20* | 6.7 |
| Pelargonidin to Pelargonidin-3-Glucoside | 42* | 8.3 |

*Reflects greater dynamic range of metabolic expression analysis

Comments: FIGS. 7 through 12 and Table IV show the power of non-targeted metabolic profiling in studying changes that occur during development. Non-Targeted metabolic profiling allows the researcher to monitor entire metabolic pathways simultaneously. There is no other methodology that allows for the simultaneous analysis of such a diverse range of analytes. All of the analytes illustrated above were extracted from the non-targeted data collected using the methodology and concepts presented in this application. and identification of unknown metabolites). Relative changes in 3-Methylsulphinylheptyl Glucosinolate illustrated.

TABLE V

Comparison of Glucosinolates in different
*Arabidopsis thaliana* mutants
Arabidopsis Glucosinolate Mutants

| | Glucosinolates | | | | |
|---|---|---|---|---|---|
| R = | WT | TU1 | TU3 | TU5 | TU7 |
| 3-Methylthiobutyl | 1.00 | <0.06(nf) | 2.69 | 0.14 | 0.36 |
| 3-Methylthiopentyl | 1.00 | <0.56(nf) | 2.12 | <0.56(nf) | 0.71 |
| 3-Methylthioheptyl | 1.00 | 1.00 | <0.21(nf) | 0.32 | <0.21(nf) |
| 3-Methylthiooctyl | 1.00 | 2.93 | <0.09(nf) | 0.92 | 0.15 |
| 3-Methylsulphinylpropyl | 1.00 | 27.62 | 1.37 | 21.56 | 0.37 |
| 3-Methylsulphinylbutyl | 1.00 | 0.10 | 2.50 | 0.63 | 0.53 |
| 3-Methylsulphinylpentyl | 1.00 | 1.56 | 3.11 | 0.79 | 1.11 |
| 3-Methylsulphinylheptyl | 1.00 | 1.38 | <0.37(nf) | 0.64 | <0.37(nf) |
| 3-Methylsulphinyloctyl | 1.00 | 6.16 | <0.11(nf) | 4.25 | 0.37 |
| 3-Indolylmethyl | 1.00 | 4.44 | 0.90 | 1.85 | 0.71 |
| Methoxy-3-Indolylmethyl | 1.00 | 1.41 | 0.67 | 0.59 | 0.46 |
| C3H7OS | 1.00 (nf) | >6.88 | nf | nf | nf |
| C5H11O8S | 1.00 | 2.68 | 0.73 | 0.85 | 0.60 |
| C7H10OS3 | 1.00 (nf) | >5.73 | nf | >3.01 | nf |
| C8H12OS3 | 1.00 | <0.37(nf) | 1.95 | <0.37(nf) | 0.45 |
| C13H26NO3S | 1.00 | 2.55 | 1.05 | 1.18 | 0.44 |
| C21H23O3 | 1.00 | 2.74 | 1.21 | 0.47 | 0.52 |

19 Glucosinolate Molecules Observed (17 reported)

Comments: In Table V, the applicability of the technology for comparing genetic mutants to their wild-type counterparts is illustrated. The non-targeted metabolic profiles of four mutants (TU1, TU3, TU5, and TU7) were compared to their wild-type counterpart. Here we show that not only can we identify and monitor the glucosinolates that had been previously analyzed using targeted analysis, but were able to identify previously unidentified glucosinolates. As is the case in all of our analyses, all of the other metabolites are also available for evaluation.

TABLE VI

Illustration of database generated by directly comparing two samples (carrot root exuate in the presence and absence of phosphate) Summary of Metabolites that were Observed to be Increased in the −P Fraction

| −P/+P Ratio (Corr.) | Mode | Minus P | | | Plus P | | Proposed Empirical Formula | |
|---|---|---|---|---|---|---|---|---|
| | | Mass | Abs Int. | Corr. Int. | Mass | Abs Int. | C | H |
| 1172.550 | ESI+ | 245.0783 | 2.35E+09 | 1.17E+09 | | 1.00E+06 | 10 | 9 |
| 1053.350 | ESI+ | 467.1672 | 2.11E+09 | 1.05E+09 | | 1.00E+06 | 22 | 23 |
| 981.550 | ESI+ | 177.0546 | 1.95E+09 | 9.82E+08 | | 1.00E+06 | 10 | |
| 658.650 | ESI+ | 223.0965 | 1.32E+09 | 6.59E+08 | | 1.00E+06 | 12 | |
| 186.090 | ESI+ | 261.0524 | 3.72E+08 | 1.86E+08 | | 1.00E+06 | 12 | |
| 73.375 | ESI+ | 651.2412 | 1.47E+08 | 7.34E+07 | | 1.00E+06 | 31 | 35 |
| 52.845 | ESI+ | 328.1390 | 1.06E+08 | 5.28E+07 | | 1.00E+06 | 15 | 22 |
| 47.308 | ESI+ | 619.2509 | 9.46E+07 | 4.73E+07 | | 1.00E+06 | 31 | 35 |
| 35.421 | ESI+ | 559.3239 | 7.08E+07 | 3.54E+07 | | 1.00E+06 | 28 | 43 |
| 34.279 | ESI+ | 539.2613 | 6.86E+07 | 3.43E+07 | | 1.00E+06 | 27 | 35 |
| 31.780 | ESI+ | 307.0489 | 6.36E+07 | 3.18E+07 | | 1.00E+06 | 12 | 19 |
| 28.136 | ESI+ | 523.2299 | 5.63E+07 | 2.81E+07 | | 1.00E+06 | 26 | 31 |
| 25.510 | ESI+ | 569.1988 | 5.10E+07 | 2.55E+07 | | 1.00E+06 | 26 | 29 |
| 24.248 | ESI− | 279.1236 | 2.42E+07 | 2.42E+07 | | 1.00E+06 | 15 | 19 |
| 22.393 | ESI+ | 635.3554 | 4.48E+07 | 2.24E+07 | | 1.00E+06 | 34 | 47 |
| 21.312 | ESI+ | 543.3288 | 4.26E+07 | 2.13E+07 | | 1.00E+06 | 28 | 43 |
| 20.003 | APCI+ | 377.1594 | 2.00E+07 | 2.00E+07 | | 1.00E+06 | 20 | 25 |
| 19.937 | ESI+ | 291.0714 | 3.99E+07 | 1.99E+07 | | 1.00E+06 | 11 | 15 |
| 15.314 | APCI− | 279.1239 | 1.53E+07 | 1.53E+07 | | 1.00E+06 | 15 | 19 |
| 13.322 | ESI+ | 487.2663 | 2.66E+07 | 1.33E+07 | | 1.00E+06 | 24 | 35 |
| 13.273 | ESI− | 335.2227 | 6.63E+07 | 6.63E+07 | 335.2227 | 5.00E+06 | 20 | 31 |
| 13.091 | APCI− | 335.2230 | 1.60E+08 | 1.60E+08 | 335.2231 | 1.22E+07 | 20 | 31 |
| 12.968 | ESI+ | 242.0700 | 2.59E+07 | 1.30E+07 | | 1.00E+06 | 15 | 20 |
| 11.693 | ESI+ | 473.2507 | 2.34E+07 | 1.17E+07 | | 1.00E+06 | 23 | 33 |
| 11.236 | ESI− | 167.6111 | 1.12E+07 | 1.12E+07 | | 1.00E+06 | 18 | 29 |
| 9.001 | ESI+ | 149.0233 | 4.81E+08 | 2.40E+08 | 149.0233 | 2.67E+07 | 8 | 5 |
| 8.226 | ESI+ | 459.2352 | 1.65E+07 | 8.23E+06 | | 1.00E+06 | 22 | 31 |
| 8.011 | APCI+ | 319.2267 | 3.59E+07 | 3.59E+07 | 319.2267 | 4.48E+06 | 20 | 31 |
| 7.742 | ESI− | 249.1494 | 2.14E+07 | 2.14E+07 | 249.1494 | 2.77E+06 | 15 | 21 |

TABLE VI-continued

Illustration of database generated by directly comparing two samples (carrot root exuate in the presence and absence of phosphate) Summary of Metabolites that were Observed to be Increased in the −P Fraction

| | | | | | | | | |
|---|---|---|---|---|---|---|---|---|
| 7.279 | ESI− | 333.2071 | 1.43E+07 | 1.43E+07 | 333.2071 | 1.96E+06 | 20 | 29 |
| 7.163 | ESI+ | 483.1415 | 1.43E+07 | 7.16E+06 | | 1.00E+06 | 24 | 28 |
| 6.902 | ESI− | 347.1864 | 1.15E+07 | 1.15E+07 | 347.1864 | 1.66E+06 | 20 | 27 |
| 6.655 | APCI− | 263.1290 | 6.66E+06 | 6.66E+06 | | 1.00E+06 | 15 | 19 |
| 6.270 | APCI− | 347.1867 | 1.87E+07 | 1.87E+07 | 347.1867 | 2.98E+06 | 20 | 27 |
| 6.019 | ESI+ | 345.1258 | 1.20E+07 | 6.02E+06 | | 1.00E+06 | 14 | 22 |
| 5.306 | ESI− | 263.1287 | 5.31E+06 | 5.31E+06 | | 1.00E+06 | 15 | 19 |
| 5.300 | ESI+ | 229.1047 | 1.06E+07 | 5.30E+06 | | 1.00E+06 | 15 | 17 |
| 4.971 | ESI− | 191.1076 | 4.97E+06 | 4.97E+06 | | 1.00E+06 | 12 | 15 |
| 4.603 | ESI− | 213.1494 | 2.32E+07 | 2.32E+07 | 213.1494 | 5.03E+06 | 12 | 21 |
| 4.600 | ESI− | 277.1443 | 4.60E+06 | 4.60E+06 | | 1.00E+06 | 16 | 21 |
| 4.524 | APCI− | 333.2074 | 2.20E+07 | 2.20E+07 | 333.2075 | 4.87E+06 | 20 | 29 |
| 4.163 | ESI− | 199.1341 | 1.18E+07 | 1.18E+07 | 199.1341 | 2.83E+06 | 11 | 19 |
| 3.392 | ESI− | 227.1650 | 3.17E+07 | 3.17E+07 | 227.1650 | 9.33E+06 | 13 | 23 |
| 3.131 | ESI+ | 312.1441 | 6.26E+06 | 3.13E+06 | | 1.00E+06 | 15 | 22 |
| 3.111 | APCI− | 249.1497 | 1.54E+07 | 1.54E+07 | 249.1497 | 4.95E+06 | 15 | 21 |
| 2.566 | APCI− | 329.2336 | 2.29E+07 | 2.29E+07 | 329.2335 | 8.92E+06 | 18 | 33 |
| 2.438 | ESI− | 415.1794 | 2.44E+06 | 2.44E+06 | | 1.00E+06 | 20 | 31 |
| 2.017 | ESI+ | 285.0951 | 4.03E+06 | 2.02E+06 | | 1.00E+06 | 10 | 17 |

| −P/+P Ratio (Corr.) | Mode | \multicolumn{8}{c}{Proposed Empirical Formula} | Observed As | Theoretical Mass | Error (ppm) |

| −P/+P Ratio (Corr.) | Mode | N | O | P | S | Cl | Na | K | e¹ | As | Theoretical Mass | Error (ppm) |
|---|---|---|---|---|---|---|---|---|---|---|---|---|
| 1172.550 | ESI+ | 6 | 2 | | | | | | −1 | +H | 245.07815 | 0.73 |
| 1053.350 | ESI+ | 6 | 6 | | | | | | −1 | +H | 467.1673589 | −0.45 |
| 981.550 | ESI+ | 9 | 3 | | | | | | −1 | +H | 177.0546206 | −0.17 |
| 658.650 | ESI+ | 15 | 4 | | | | | | −1 | +H | 223.0964854 | −0.16 |
| 186.090 | ESI+ | 14 | 4 | | | | 1 | | −1 | +K | 261.0523672 | 0.05 |
| 73.375 | ESI+ | 6 | 10 | | | | | | −1 | +H | 651.2409178 | 0.48 |
| 52.845 | ESI+ | 1 | 7 | | | | | | −1 | +H | 328.1390785 | −0.24 |
| 47.308 | ESI+ | 6 | 8 | | | | | | −1 | +H | 619.2510685 | −0.39 |
| 35.421 | ESI+ | 6 | 6 | | | | | | −1 | +H | 559.3238596 | 0.13 |
| 34.279 | ESI+ | 6 | 6 | | | | | | −1 | +H | 539.2612593 | 0.00 |
| 31.780 | ESI+ | | 3 | | 3 | | | | −1 | +H | 307.049083 | −0.60 |
| 28.136 | ESI+ | 6 | 6 | | | | | | −1 | +H | 523.2299592 | −0.09 |
| 25.510 | ESI+ | 8 | 9 | | | | | | −1 | +H | 569.199053 | −0.44 |
| 24.248 | ESI− | | 5 | | | | | | 1 | −H | 279.1237973 | −0.60 |
| 22.393 | ESI+ | 6 | 6 | | | | | | −1 | +H | 635.3551597 | 0.36 |
| 21.312 | ESI+ | 6 | 5 | | | | | | −1 | +H | 543.3289449 | −0.21 |
| 20.003 | APCI+ | | 7 | | | | | | −1 | +H | 377.1594796 | −0.18 |
| 19.937 | ESI+ | | 9 | | | | | | −1 | +H | 291.0710585 | 1.04 |
| 15.314 | APCI− | | 5 | | | | | | 1 | −H | 279.1237973 | 0.26 |
| 13.322 | ESI+ | 6 | 5 | | | | | | −1 | +H | 487.2663447 | −0.07 |
| 13.273 | ESI− | | 4 | | | | | | 1 | −H | 335.2227831 | −0.40 |
| 13.091 | APCI− | | 4 | | | | | | 1 | −H | 335.2227831 | 0.66 |
| 12.968 | ESI+ | 10 | 9 | | | | | | −2 | +2H | 242.0701876 | −0.86 |
| 11.693 | ESI+ | 8 | 5 | | | | | | −1 | +H | 473.2506946 | 0.10 |
| 11.236 | ESI− | 3 | 3 | | | | | | 2 | −2H | 167.6109945 | 0.33 |
| 9.001 | ESI+ | | 3 | | | | | | −1 | +H | 149.0233204 | 0.00 |
| 8.226 | ESI+ | 6 | 5 | | | | | | −1 | +H | 459.2350446 | 0.36 |
| 8.011 | APCI+ | | 3 | | | | | | −1 | +H | 319.2267713 | −0.22 |
| 7.742 | ESI− | | 3 | | | | | | 1 | −H | 249.1496181 | −0.71 |
| 7.279 | ESI− | | 4 | | | | | | 1 | −H | 333.207133 | −0.13 |
| 7.163 | ESI+ | | 8 | | | | 1 | | −1 | +K | 463.1415762 | −0.12 |
| 6.902 | ESI− | | 5 | | | | | | 1 | −H | 347.1863976 | −0.11 |
| 6.655 | APCI− | | 4 | | | | | | 1 | −H | 263.1288827 | 0.26 |
| 6.270 | APCI− | | 5 | | | | | | 1 | −H | 347.1863976 | 0.83 |
| 6.019 | ESI+ | 6 | | 1 | | | 1 | | −1 | +K | 345.1258237 | −0.01 |
| 5.306 | ESI− | | 4 | | | | | | 1 | −H | 263.1288827 | −0.69 |
| 5.300 | ESI+ | | | 1 | | | | | −1 | +H | 229.1045477 | 0.75 |
| 4.971 | ESI− | 2 | | | | | | | 1 | −H | 191.1077533 | −0.80 |
| 4.603 | ESI− | | 3 | | | | | | 1 | −H | 213.1496181 | −1.02 |
| 4.600 | ESI− | | 4 | | | | | | 1 | −H | 277.1445327 | −0.84 |
| 4.524 | APCI− | | 4 | | | | | | 1 | −H | 333.207133 | 0.97 |
| 4.163 | ESI− | | 3 | | | | | | 1 | −H | 199.1339681 | 0.61 |
| 3.392 | ESI− | | 3 | | | | | | 1 | −H | 227.1652682 | −1.05 |
| 3.131 | ESI+ | 1 | 6 | | | | | | −1 | +H | 312.1441639 | −0.08 |
| 3.111 | APCI− | | 3 | | | | | | 1 | −H | 249.1496181 | 0.19 |
| 2.566 | APCI− | | 5 | | | | | | 1 | −H | 329.2333477 | 0.58 |
| 2.438 | ESI− | | 7 | 1 | | | | | 1 | −H | 415.1795976 | −0.50 |
| 2.017 | ESI+ | 6 | | 2 | | | | | −1 | +H | 285.0950624 | −0.01 |

Comments: Table VI illustrates how our technology can be used to compare the metabolic profile of an organism under different environmental conditions. Here we were able to detect and identify key molecules involved in controlling the plant's response to phosphate conditions. This capability allows researchers to determine what effects changes in environmental conditions will have on the biological functions of an organism.

TABLE VII

MS/MS Data for Selected Metabolites Observed to be Increased in the-P Fraction

| Parent | Fragment | Loss Of: |
|---|---|---|
| $C_{31}H_{35}N_6O_{10}[H^+]$ 651 + ESI | $C_{19}H_{23}N_6O_5[H^+]$ $C_{19}H_{21}N_6O_4[H^+]$ *$C_{10}H_9N_6O_2[H^+]$ $C_9H_7[H^+]$ | $C_{12}H_{12}O_5$ $C_{12}H_{14}O_6$ $C_{21}H_{24}O_8$ |
| $C_{31}H_{35}N_6O_8[H^+]$ 619 + ESI | $C_{19}H_{23}N_6O_5[H^+]$ $C_{19}H_{21}N_6O_4[H^+]$ *$C_{10}H_9N_6O_2[H^+]$ $C_9H_7[H^+]$ | $C_{12}H_{12}O_3$ $C_{12}H_{14}O_4$ $C_{21}H_{24}O_6$ |
| $C_{26}H_{29}N_6O_9[H^+]$ 569 + ESI | $C_{19}H_{23}N_6O_5[H^+]$ $C_{19}H_{21}N_6O_4[H^+]$ *$C_{10}H_9N_6O_2[H^+]$ $C_9H_7[H^+]$ | $C_7H_6O_4$ $C_7H_8O_5$ $C_{16}H_{20}O_7$ |
| $C_{28}H_{43}N_6O_6[H^+]$ 559 + ESI | $C_{19}H_{23}N_6O_5[H^+]$ $C_{19}H_{21}N_6O_4[H^+]$ *$C_{10}H_9N_6O_2[H^+]$ $C_9H_7[H^+]$ | $C_9H_{20}O$ $C_9H_{22}O_2$ $C_{18}H_{20}O_4$ |
| $C_{28}H_{43}N_6O_5[H^+]$ 543 + ESI | $C_{19}H_{23}N_6O_5[H^+]$ $C_{19}H_{21}N_6O_4[H^+]$ *$C_{10}H_9N_6O_2[H^+]$ $C_9H_7[H^+]$ | $C_9H_{20}$ $C_9H_{22}O$ $C_{18}H_{20}O_3$ |
| $C_{27}H_{35}N_6O_6[H^+]$ 539 + ESI | $C_{19}H_{23}N_6O_5[H^+]$ $C_{19}H_{21}N_6O_4[H^+]$ *$C_{15}H_{21}N_6O_2[H^+]$ $C_{10}H_9N_6O_2[H^+]$ $C_9H_7[H^+]$ | $C_8H_{12}O$ $C_8H_{14}O_2$ *$C_{12}H_{14}O_4$ $C_{17}H_{26}O_4$ |
| $C_{26}H_{31}N_6O_6[H^+]$ 523 + ESI | $C_{19}H_{23}N_6O_5[H^+]$ $C_{19}H_{21}N_6O_4[H^+]$ *$C_{14}H_{17}N_6O_2[H^+]$ $C_{10}H_9N_6O_2[H^+]$ $C_9H_7[H^+]$ | $C_7H_9O$ $C_7H_{10}O_2$ *$C_{12}H_{14}O_4$ $C_{16}H_{22}O_4$ |
| $C_{22}H_{23}N_6O_6[H^+]$ 467 + ESI | *$C_{10}H_9N_6O_2[H^+]$ | *$C_{12}H_{14}O_4$ |
| *$C_{12}H_{15}O_4[H^+]$ 223 + ESI | *$C_{10}H_9O_3[H^+]$ $C_9H_7O_3[H^+]$ $C_8H_5O_3[H^+]$ $C_6H_5O[H^+]$ | $C_2H_6O$ $C_3H_8O$ $C_4H_{10}O$ $C_6H_{10}O_3$ |
| *$C_{10}H_9O_3[H^+]$ 177 + ESI | *$C_8H_5O_3[H^+]$ $C_6H_5O[H^+]$ | $C_2H_4$ $C_4H_4O_2$ |
| *$C_8H_5O_3[H^+]$ 149 + ESI | $C_7H_5O_2[H^+]$ $C_6H_5O[H^+]$ | CO $C_2O_2$ |

TABLE VIII

Determination of Metabolite Relations using MS/MS data

| R1 | R3 | R2 |
|---|---|---|
| $C_{10}H_8N_6O_2$ | None | $C_{12}H_{14}O_4$ |
| $C_{10}H_8N_6O_2$ | $C_4H_8$ | $C_{12}H_{14}O_4$ |
| $C_{10}H_8N_6O_2$ | $C_5H_{12}$ | $C_{12}H_{14}O_4$ |
| $C_{10}H_8N_6O_2$ | $C_6H_6$ | $C_{12}H_{14}O_4$ |
| $C_{10}H_8N_6O_2$ | $C_4H_6O_3$ | $C_{12}H_{14}O_4$ |
| $C_{10}H_8N_6O_2$ | $C_9H_{10}O_2$ | $C_{12}H_{14}O_4$ |
| $C_{10}H_8N_6O_2$ | $C_9H_{10}O_4$ | $C_{12}H_{14}O_4$ |
| $C_{10}H_8N_6O_2$ | $C_6H_6$ | $C_{12}H_{14}O_3$ |

TABLE IX

Mass Analysis of unknown peak observed in Tobacco Flower Analysis

Mass Analysis of Unknown Peak
Calibration Constants:

| ML1: | 108299134.679450 |
|---|---|
| ML2: | −16.576817 |
| ML3: | −2029.796744 |

Calibration Results:

| Ref. Masses | Exp. Masses | Diff (ppm) |
|---|---|---|
| 124.039300 | 124.039298 | 0.0187 |
| 161.092070 | 161.092079 | 0.0542 |
| 303.166300 | 303.166272 | 0.0919 |
| 609.280660 | 609.280664 | 0.0060 |
| 962.430130 | 962.430230 | 0.1037 |

Observed Mass of Unknown: 595.16572
Empirical Formula Search Result: $C_{27}H_{30}O_{15}$ [+H]+
Mass: 595.16575
Mass Error: 0.04 ppm
Proposed Metabolite: $C_{15}H_{10}O_6$ - Rhamnoglucoside
(present in flowers of grapefruit)

Figure 16:
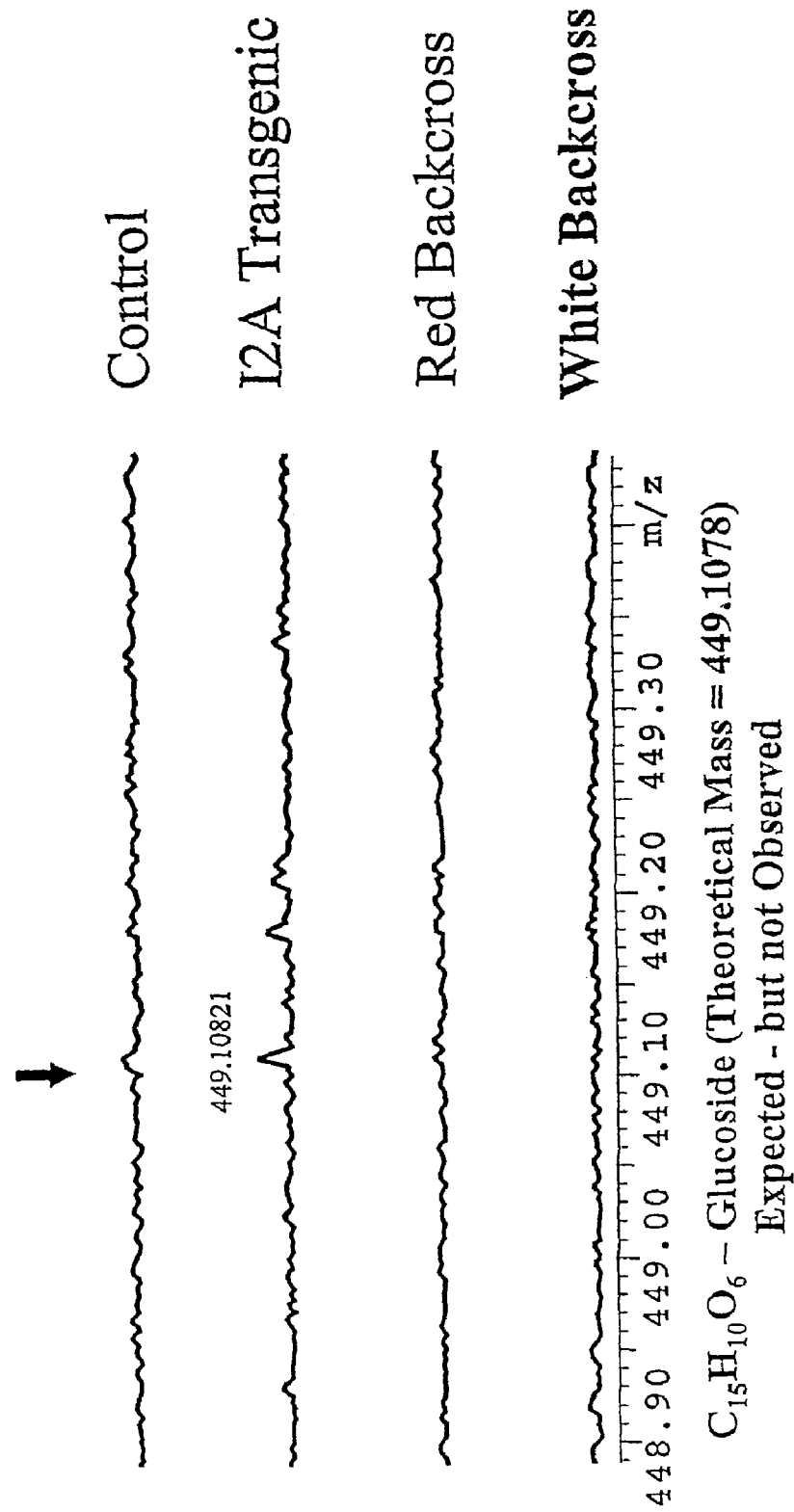
FIG. 16 is an illustration of Tobacco Flower Analysis (Location of metabolite expected to be responsible for red color in tobacco).
Figure 17:
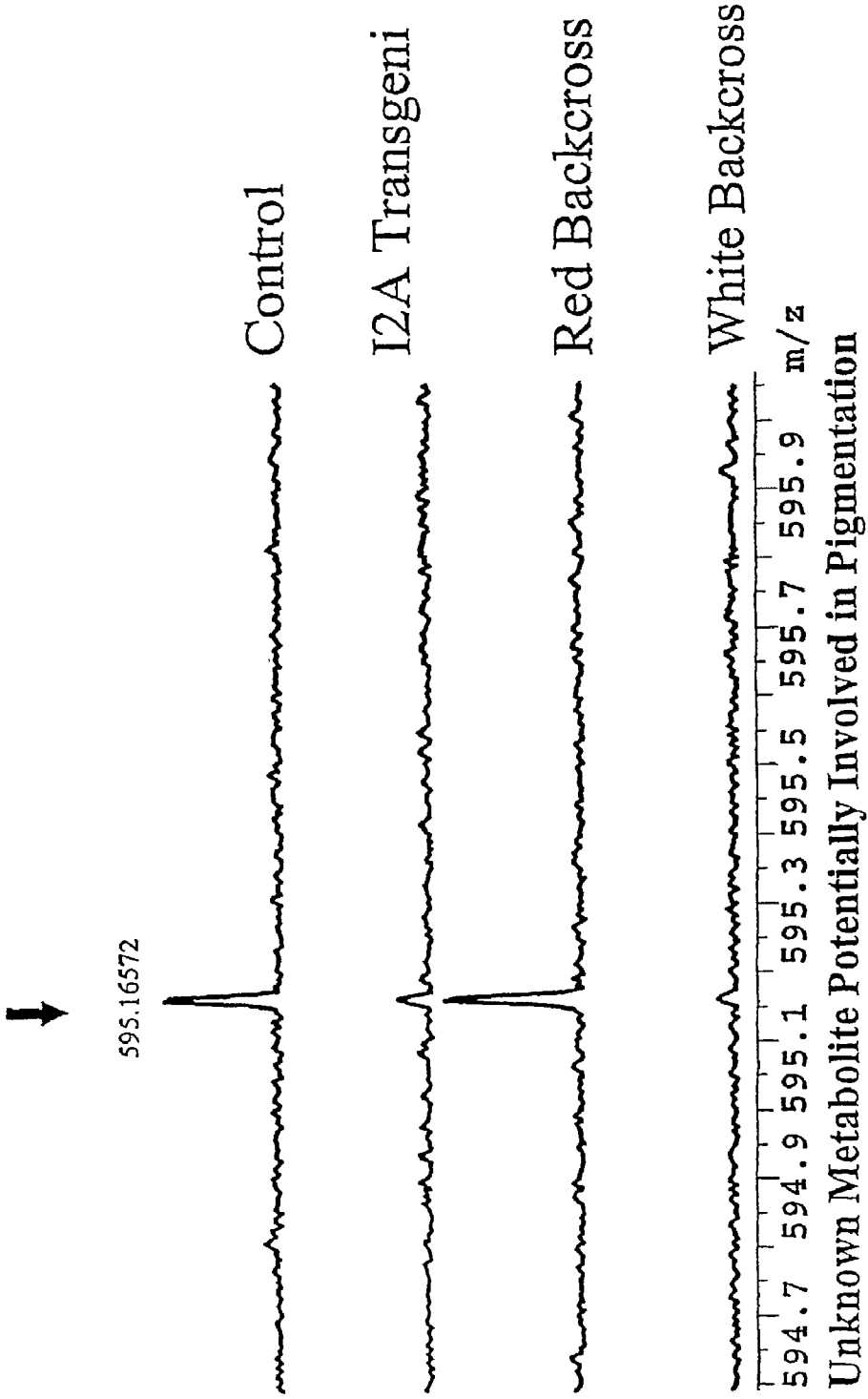
FIG. 17 is an illustration of Tobacco Flower Analysis (Location of unknown metabolite potentially involved in tobacco color).

Comments: FIGS. 16 and 17 and Table 1×show how our technology provides meaningful information that would otherwise not be obtained. In this example the researcher thought that he knew the primary color component in tobacco flowers (C15H10O6-Glucoside) but our analysis showed that the primary color component in tobacco flowers is actually the rhamnoglucoside. This illustrates the power of being able to identify unknown components after analysis. No other technology is currently available to provide this type of analysis.

TABLE X

Illustration of the number of metabolites monitored in strawberry extracts. Summary of Metabolites Observed from Different Extraction Methods and Ionization Conditions.

| | Number of Unique Metabolites Observed | | | |
|---|---|---|---|---|
| | 50/50 | ACN | In Both | Total |
| ESI + | 1143 | 1054 | 540 | 1657 |
| ESI − | 966 | 790 | 211 | 1545 |
| APCI + | 979 | 1431 | 615 | 1795 |
| APCI − | 898 | 1205 | 370 | 1733 |
| Total | 3986 | 4480 | 1736 | 6730 |

Figure 18:
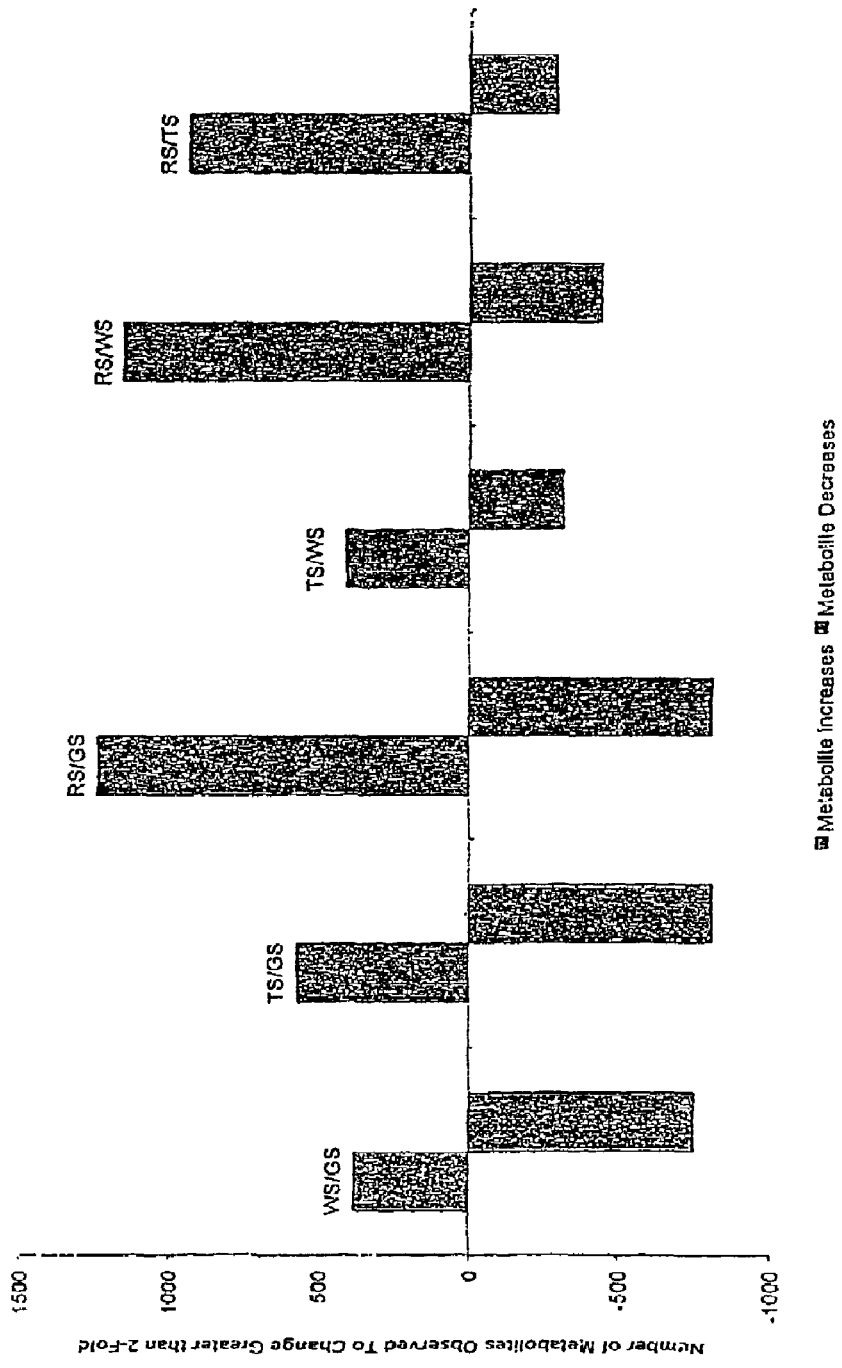
FIG. 18 is an illustration of Observed Metabolic Changes in Strawberry Development.

Table X and FIG. 18 illustrate the comprehensive nature of our invention. Our technology allows for the comprehensive comparison of the metabolic profiles of organisms under varying environmental, genetic, and developmental conditions.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

It will be apparent to one skilled in the art that modifications may be made to the illustrated embodiment without departing from the spirit and scope of the invention as hereinafter defined in the claims.

The embodiments of the invention in which an exclusive property or privilege is claimed are defined as follows:

1. A method for analysis of a plurality of biological samples to identify one or more unidentified metabolites of different intensities between samples, comprising the steps of:
   a) introducing the plurality of biological samples, each of which contains a plurality of unidentified metabolites without any a priori selection of metabolites of interest, into a Fourier Transform Ion Cyclotron Resonance Mass Spectrometer (FTMS);
   b) simultaneously obtaining, identifying and quantifying data for the plurality of unidentified metabolites detected in each of the biological samples introduced into the FTMS, wherein the identifying data comprise accurate mass and the quantifying data are intensity data;
   c) creating a database comprising said identifying and quantifying data;
   d) analyzing the database to determine metabolites of different intensities between samples; and
   e) identifying one or more unidentified metabolites so determined by a method selected from the group consisting of matching the identifying data of the unidentified metabolites to identifying data of known metabolites, determining the empirical formula of the one or more unidentified metabolites, and analyzing the MS/MS fragment data of the one or more unidentified metabolites.

2. The method as defined in claim 1, wherein each of the biological samples is a biological extract of metabolites.

3. The method as defined in claim 1, wherein the accurate mass is used to calculate the empirical formula of the one or more than one unidentified metabolites.

4. The method as defined in claim 3, wherein the database created in step c) of claim 1 is organized to permit searching for one or more known metabolites by empirical formula.

5. The method as defined in claim 1, wherein the database created in step c) of claim 1 is organized to permit searching for one or more known metabolites by accurate mass.

6. The method as defined in claim 3, wherein the database created in step c) of claim 1 is organized to permit identification of unknown metabolites by the empirical formulae of the metabolites.

7. The method as defined in claim 1, wherein the database created in step c) of claim 1 is organized to permit the comparison of one or more test samples to one or more control samples such that the intensity of metabolites present in the test samples can be determined relative to the control samples and other test samples.

8. The method as defined in claim 1, wherein the FTMS is used with a chromatographic separation system.

9. The method as defined in claim 1, wherein the FTMS is equipped with a soft ionization source.

10. The method as defined in claim 1, wherein the FTMS is equipped with an additional mass selective pre-separation system.

11. The method as defined in claim 1, wherein the identifying and quantifying data from said biological samples are obtained from a genetically modified test organism and a non genetically modified control organism and the identifying and quantifying data obtained from said biological samples are further correlated with gene expression data from same said organisms for the purpose of determining the function of the genes affected by the genetic modification.

12. The method as defined in claim 1, wherein the identifying and quantifying data from said biological samples are obtained from an organism exposed to a test environment and an organism exposed to a control environment and the identifying and quantifying data obtained from said biological samples are further correlated with gene expression data obtained from same said organisms under same said conditions for the purpose of determining the function of the genes affected by the test environment.

13. The method as defined in claim 12, wherein the test environment is an internal or external force imparted on the organism.

14. The method as defined in claim 13, wherein the internal or external force comprises exposure to or withdrawal from a chemical, weather conditions, or psychological conditions.

15. The method as defined in claim 1, wherein the identifying and quantifying data from said biological samples are obtained from an organism at different stages of its development and the identifying and quantifying data obtained from said biological samples are farther correlated with gene expression data from same said organism under same said stages of development for the purpose of determining the function of the genes affected by the changes in development of the organism.

16. The method as defined in claim 1, wherein the database created in step c) of claim 1 is organized to permit the comparison of any two or more samples to each other, such that the presence or absence of an intensity of metabolites found in some samples but not in others is determined.

17. The method as defined in claim 1, wherein the database created in step c) of claim 1 is organized to permit the comparison of one or more test samples to one or more control samples such that the presence or absence of an intensity of metabolites present in the test samples can be determined relative to the control samples or other test samples.

18. A method for the analysis of a plurality of biological samples to identify one or more unidentified metabolites of different intensities between samples, comprising the steps of:
   a) injecting a plurality of biological samples, each of which contains a plurality of unidentified metabolites without any a priori selection of metabolites of interest, into a Fourier Transform Ion Cyclotron Mass Spectrometer with or without the additional use of a chromatographic column;
   b) ionizing the metabolites using a soft ionization source;
   c) transferring the ionized metabolites to an ion cyclotron resonance (ICR) cell with or without additional mass selective pre-separation;
   d) separating and measuring said ions in the ICR cell with or without simultaneous MS/MS analysis occurring;
   e) simultaneously determining accurate mass and intensity data of each of the ions detected;
   f) transferring said data to a database that stores and organizes the data;
   g) comparing intensity data of the biological samples contained within the database to one another to determine metabolites of different intensities as between samples; and
   h) identifying one or more unidentified metabolites so determined, by a method selected from the group consisting of matching the accurate mass data of the unidentified metabolites to accurate mass data of known metabolites, calculating the empirical formula of the one or more unidentified metabolites, and analyzing the MS/MS fragment data of the one or more unidentified metabolites.

19. A method for analysis of a plurality of biological samples to identify one or more unidentified metabolites from said samples when compared with a database of known metabolites, comprising the steps of:
  a) introducing a plurality of biological samples, each of which contains a plurality of unidentified metabolites without any a priori selection of metabolites of interest, into a Fourier Transform Ion Cyclotron Resonance Mass Spectrometer (FTMS);
  b) simultaneously obtaining, identifying and quantifying data for the plurality of unidentified metabolites detected in each of the biological samples introduced into the FTMS, wherein the identifying data comprise accurate mass data and the quantifying data are intensity data;
  c) creating a database comprising said identifying and quantifying data;
  d) comparing the identifying and quantifying data of the said database with a known database containing identifying and quantifying data of known metabolites; and
  e) identifying one or more unidentified metabolites so compared by matching said identifying data of unidentified metabolites to said identifying data of known metabolites.

20. A method for analysis of a plurality of biological samples to create and organize a database by metabolic concentration, comprising the steps of:
  a) introducing a plurality of biological samples, each of which contains a plurality of unidentified metabolites without any a priori selection of metabolites of interest, into a Fourier Transform Ion Cyclotron Resonance Mass Spectrometer (FTMS);
  b) simultaneously obtaining, identifying and quantifying data for the plurality of unidentified metabolites detected in each of the biological samples introduced into the FTMS, wherein the identifying data comprise accurate mass data and the quantifying data are intensity data;
  c) creating a database comprising said identifying and quantifying data; and
  d) organizing the database by metabolic concentration.

21. A method for analysis of a plurality of biological samples, comprising the steps of:
  a) introducing a plurality of biological samples, each of which contains a plurality of unidentified metabolites without any a priori selection of metabolites of interest, into a Fourier Transform Ion Cyclotron Resonance Mass Spectrometer (FTMS);
  b) simultaneously obtaining, identifying and quantifying data for the plurality of unidentified metabolites detected in each of the biological samples introduced into the FTMS, wherein the identifying data comprise accurate mass data and the quantifying data are intensity data;
  c) creating a database of unidentified metabolites comprising said identifying and quantifying data; and
  d) analyzing the database of unidentified metabolites, wherein the analyzing step is selected from the group consisting of:
  (i) analyzing the database of unidentified metabolites to determine metabolites of different intensities between samples and identifying one or more metabolites so determined using the identifying data by matching to a known database of known metabolites, or by the empirical formula of the one or more than one unidentified metabolites, or by the MS/MS fragment data of the one or more than one unidentified metabolites;
  (ii) comparing the database of the unidentified metabolites with a known database of known metabolites and identifying one or more metabolites so compared using the identifying data and matching said identifying data to said known database of known metabolites; and
  (iii) organizing the database of the unidentified metabolites by metabolite concentration.

* * * * *